United States Patent
Lin et al.

(10) Patent No.: US 9,823,242 B2
(45) Date of Patent: Nov. 21, 2017

(54) SENSOR STRIP AND MANUFACTURE METHOD THEREOF AND SYSTEM THEREOF

(71) Applicant: APEX BIOTECHNOLOGY CORP., Hsinchu (TW)

(72) Inventors: Ting En Lin, Taipei (TW); Chong Chien Tay, Hsinchu (TW)

(73) Assignee: APEX BIOTECHNOLOGY CORP., Hsinchu (TW)

(*) Notice: Subject to any disclaimer, the term of this patent is extended or adjusted under 35 U.S.C. 154(b) by 0 days.

(21) Appl. No.: 14/821,081

(22) Filed: Aug. 7, 2015

(65) Prior Publication Data
US 2017/0038399 A1 Feb. 9, 2017

(51) Int. Cl.
*G01N 27/00* (2006.01)
*G01N 15/06* (2006.01)
*G01N 33/00* (2006.01)
*G01N 33/543* (2006.01)

(52) U.S. Cl.
CPC ................................. *G01N 33/5438* (2013.01)

(58) Field of Classification Search
CPC ........ G01N 27/00; G01N 15/06; G01N 33/92; G01N 33/00; G01N 33/66; G01N 33/48; B01L 3/00; B01J 19/12; C12Q 1/00

USPC ... 422/82.01, 68.1, 417, 420, 502, 503, 554; 600/300; 436/43; 204/193, 403.03
See application file for complete search history.

(56) References Cited

U.S. PATENT DOCUMENTS

| | | | |
|---|---|---|---|
| 5,962,215 A * | 10/1999 | Douglas et al. | 435/4 |
| 7,611,621 B2 | 11/2009 | Cai et al. | |
| 8,460,524 B2 | 6/2013 | Popovich et al. | |
| 2004/0086424 A1 * | 5/2004 | Schembri | 422/58 |
| 2005/0269214 A1 * | 12/2005 | Lee | 205/777.5 |
| 2013/0084591 A1 | 4/2013 | McColl et al. | |
| 2013/0118899 A1 | 5/2013 | Chen et al. | |
| 2013/0267032 A1 * | 10/2013 | Tsai et al. | 436/95 |
| 2014/0021046 A1 | 1/2014 | Huang et al. | |

FOREIGN PATENT DOCUMENTS

TW M493052 U 1/2015

* cited by examiner

*Primary Examiner* — Brian J Sines
(74) *Attorney, Agent, or Firm* — Muncy, Geissler, Olds & Lowe, P.C.

(57) ABSTRACT

The present disclosure further provides a sensor strip. The sensor strip includes a substrate. The substrate includes a first surface, a second surface, a recess between the first surface and the second surface, and a third surface in the recess, wherein the third surface is hydrophobic. A first electrode set is disposed on top of the first surface, and a second electrode set is disposed on top of the second surface. A covering layer includes a covering surface, such as a hydrophilic surface, facing the substrate.

8 Claims, 17 Drawing Sheets

SENSOR STRIP AND MANUFACTURE METHOD THEREOF AND SYSTEM THEREOF

BACKGROUND

1. Technical Field

The present disclosure relates to a sensor strip, and more particularly, to a sensor strip having two reactive areas. Notably, the sample liquids accommodated in one reactive area do not contaminate the sample liquids accommodated in the other reactive area.

2. Background

As a result of a sumptuous diet, diseases caused by improper diet habits continuously increase. A reliable biochemical measuring system is a preferable tool for those who periodically monitor the body condition (such as blood sugar level, lipid) in daily life.

Currently on the market, many biochemical measuring systems capable of simultaneously measuring multiple biochemical concentrations has been released.

For example, a blood sugar test strip measuring both a glucose dehydrogenase (GDH) and glucose oxidase (GOD). The measuring test strip uses responses from two different glycemic indexes to check the blood sugar concentration of a user.

Another example includes multi-layer test strips. The multi-layer test strip is used to form two disconnected reactive regions.

A multi-layer test strip can achieve effects of a multi-reactive region. A first reactive region measures the blood sugar concentration. A second reactive region performs a hematocrit blood testing. The hematocrit level is used to correct the blood sugar concentration.

However, a process of manufacturing a structure of the multi-layer test strip can be complicated and increase production cost.

A single-layer test strip includes double capillary channels. By using the double capillary channels, the blood sugar level and the hematocrit level are measured separately.

A biochemical measuring system includes three reactive regions. The first reactive region detects hemoglobin and hematocrit. The second and the third reactive region measure a duration of a blood coagulation. However, the test strips including the double capillary channels and the three reactive regions have the disadvantage of using a large volume of samples, such as blood.

A biochemical measuring system includes a single channel. The single channel is separated by a spacer layer to isolate two reactive regions. The single channel reduces a bulk sample problem. However, since there are still liquid samples connecting between the two reactive regions, the liquid samples include electrical conductivity which causes interference of electrical signals between the two reactive regions, resulting in a serious measurement error.

This "Discussion of the Background" section is provided for background information only. The statements in this "Discussion of the Background" are not an admission that the subject matter disclosed in this "Discussion of the Background" section constitutes prior art to the present disclosure, and no part of this "Discussion of the Background" section may be used as an admission that any part of this application, including this "Discussion of the Background" section, constitutes prior art to the present disclosure.

SUMMARY

In order to improve the above-identified disadvantage, the present disclosure provides a sensor strip for hematocrit correction. The sensor strip includes a recess isolating two separated electrode sets in different reactive areas for measuring either hematocrit or the analytic concentration.

In accordance with the above-mentioned disadvantage, the present disclosure provides a sensor strip having two independent reactive areas which do not contaminate each other so as to reduce the signals (such as the AC signal and the DC signal) interfering at the same electrode set in the same reactive area or to reduce the signals interfering at distinct electrode sets in separated reactive areas.

One embodiment of the present disclosure further provides a sensor strip. The sensor strip comprises a substrate including a first surface, a second surface, a recess between the first surface and the second surface, and a third surface in the recess. The sensor strip further comprises a first electrode set disposed on top of the first surface, a second electrode set disposed on top of the second surface, and a covering layer comprising a covering surface facing the substrate, wherein the third surface is hydrophobic and the covering surface is hydrophilic.

The present disclosure further provides a sensor strip. The sensor strip comprises a substrate including a first surface, a second surface, and an inner surface, and a recess between the first surface and the second surface, the inner surface surrounding the recess, the inner surface being hydrophobic. The sensor strip further comprises a covering layer over the substrate, the covering layer includes a covering surface facing the substrate, and the covering surface is hydrophilic. The substrate and the covering layer forming a first reactive region disposed over the first surface and under the covering surface, and a second reactive region disposed over the second surface and under the covering surface. The sensor strip further comprises a first electrode set disposed in the first reactive region, and a second electrode set disposed in the second reactive region.

The present disclosure further provides a sensing system, comprising a sensor strip, a power source, a detector, and a microprocessor. The sensor strip comprises a substrate including a first surface, a second surface, a recess between the first surface and the second surface, and a third surface in the recess. The sensor strip further comprises a first electrode set disposed on top of the first surface, a second electrode set disposed on top of the second surface, and a covering layer comprising a covering surface facing the substrate, wherein the third surface is hydrophobic and the covering surface is hydrophilic. The power source is configured to simultaneously provide a direct current (DC) signal and an alternating current (AC) signal, wherein the DC signal is transmitted to the first electrode set, and the AC signal is transmitted to the second electrode set. The detector is configured to detect a first reactive value in response to the analyte concentration and a second reactive value in response to the hematocrit concentration. The microprocessor is configured to calculate a hematocrit-corrected analyte concentration in response to the first reactive value and the second reactive value.

The present disclosure also provides a manufacturing method of a sensor strip and the method includes the following steps: providing a substrate; forming a recess in the substrate such that the substrate comprises a first surface and a second surface separated by the recess; disposing a first electrode set at the first surface; disposing a second electrode set at the second surface; and forming a covering layer comprising a hydrophilic surface over the substrate.

The foregoing has outlined rather broadly the features and technical advantages of the present disclosure in order that the detailed description of the disclosure that follows may be better understood. Additional features and advantages of the disclosure will be described hereinafter, which form the subject of the claims of the disclosure. It should be appreciated by those skilled in the art that the conception and specific embodiment disclosed may be readily utilized as a basis for modifying or designing other structures or processes for carrying out the same purposes of the present disclosure. It should also be realized by those skilled in the art that such equivalent constructions do not depart from the spirit and scope of the disclosure as set forth in the appended claims.

BRIEF DESCRIPTION OF THE DRAWINGS

The accompanying drawings, which are incorporated in and constitute a part of this specification, illustrate embodiments of the disclosure and, together with the description, serve to explain the principles of the invention.

The foregoing summary, as well as the following detailed description of the invention, will be better understood when read in conjunction with the appended drawings. For the purpose of illustrating the invention, there are shown in the drawings examples which are presently preferred. It should be understood, however, that the invention is not limited to the precise arrangements and instrumentalities shown.

Figure 1:
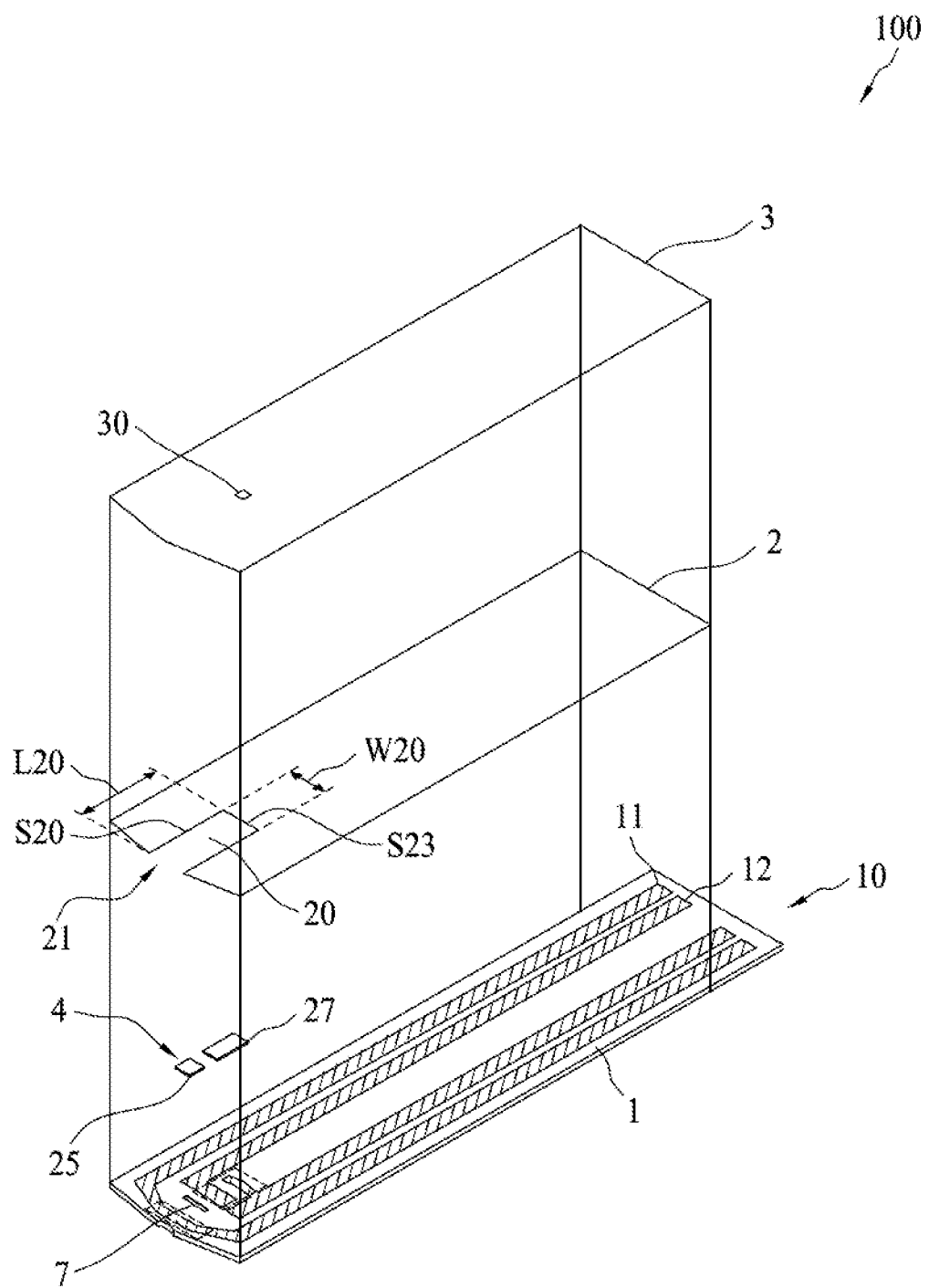
Figure 4A:
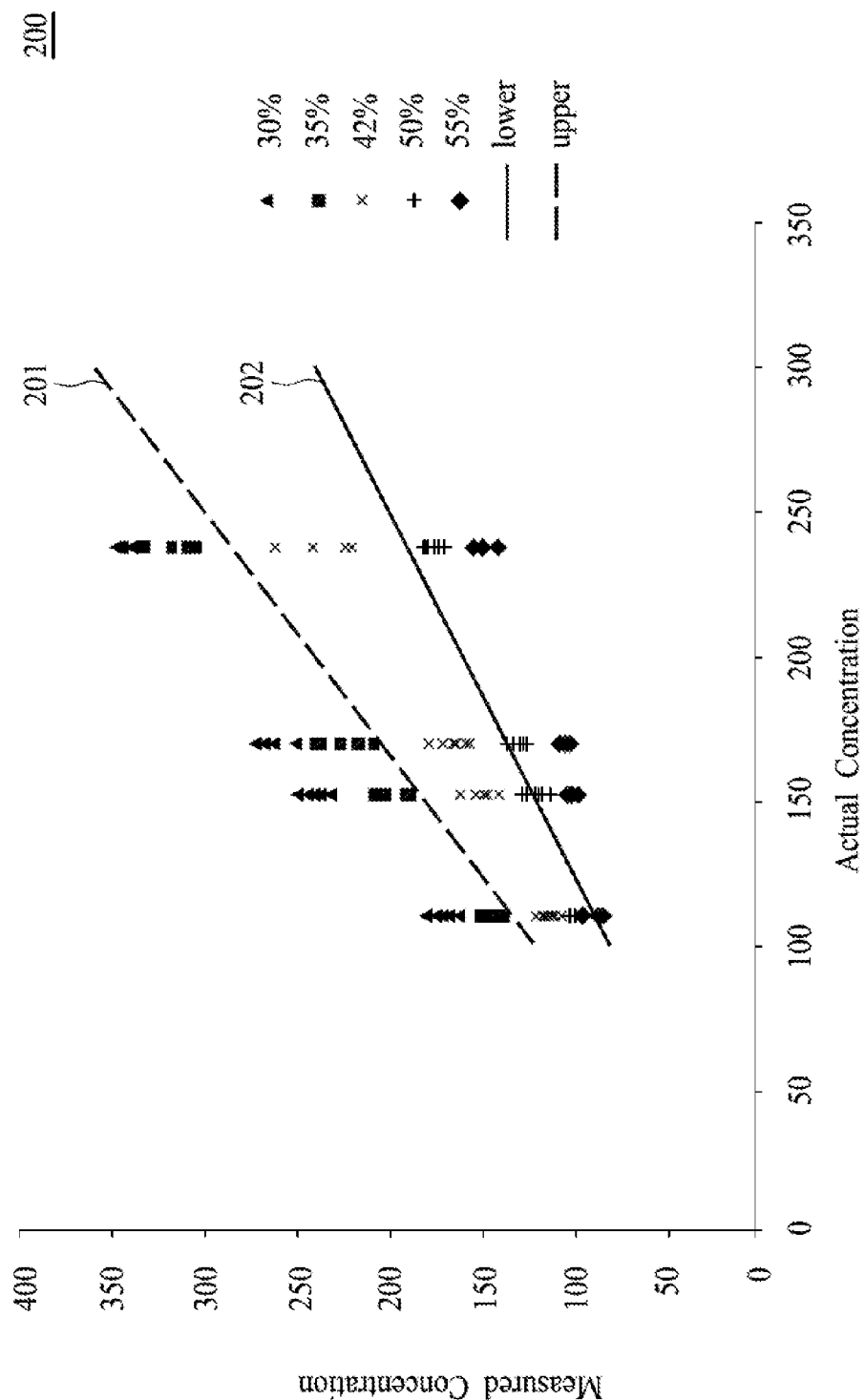
Figure 4B:
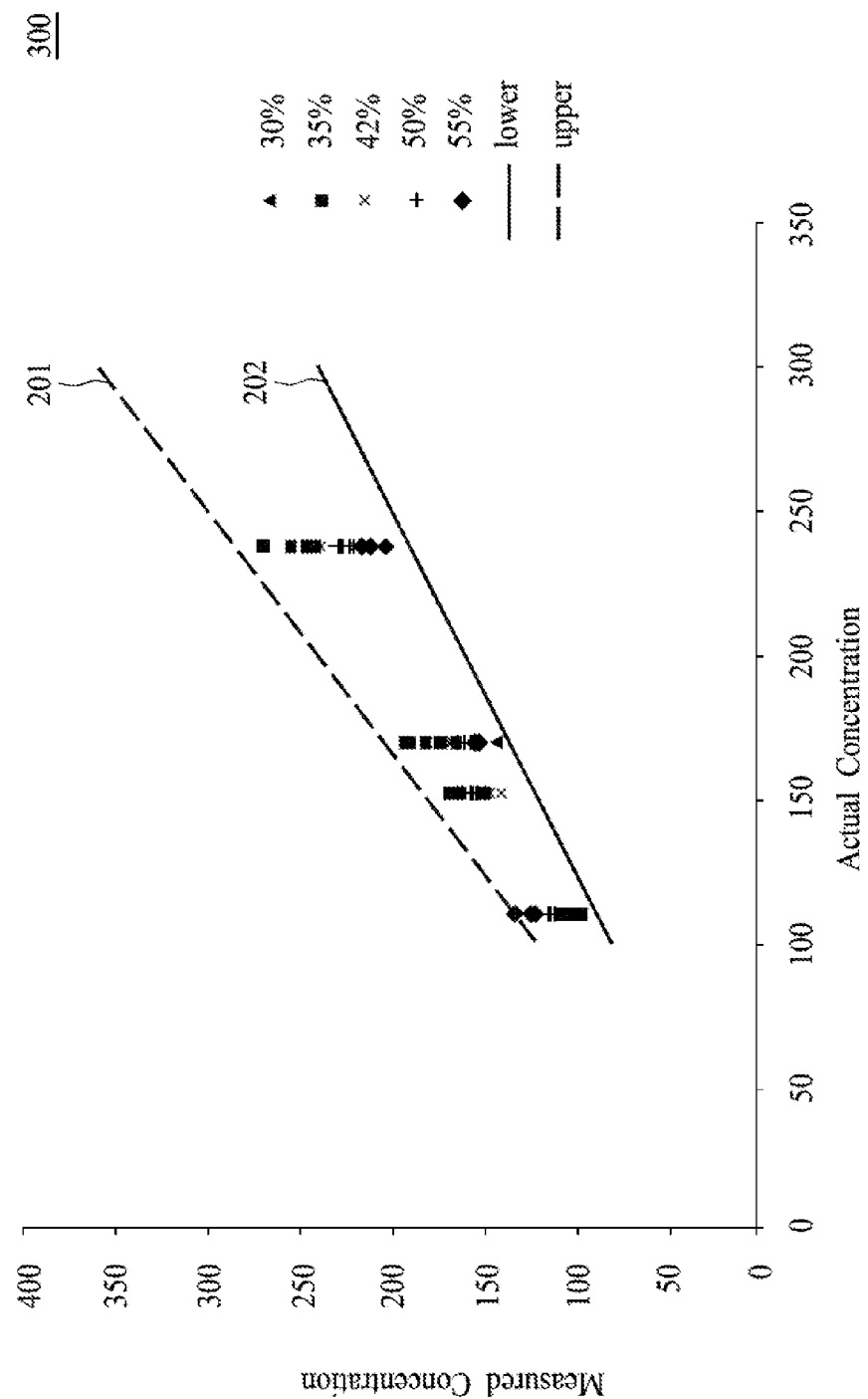

A more complete understanding of the present disclosure may be derived by referring to the detailed description and claims when considered in connection with the Figures, where like reference numbers refer to similar elements throughout the Figures, and:

FIG. 1 is a schematic view of a sensor strip in accordance with some embodiments of the present disclosure;

FIGS. 2A-2F are cross-sectional views of sensor strips in accordance with some embodiments of the present disclosure;

FIGS. 3A-3H are plan views of sensor strips in accordance with some embodiments of the present disclosure;

FIG. 4A is a diagram of a sample concentration in accordance with some embodiments of the present disclosure; and FIG. 4B is a diagram of a sample concentration in accordance with some embodiments of the present disclosure.

DETAILED DESCRIPTION

The present disclosure is directed to a sensor strip, a manufacturing method thereof and a measurement system thereof. In order to make the present disclosure completely comprehensible, detailed steps and structures are provided in the following description. Obviously, implementation of the present disclosure does not limit special details known by persons skilled in the art. In addition, known structures and steps are not described in details, so as not to limit the present disclosure unnecessarily. Preferred embodiments of the present disclosure will be described below in detail. However, in addition to the detailed description, the present disclosure may also be widely implemented in other embodiments. The scope of the present disclosure is not limited to the detailed embodiments, and is defined by the claims.

The following description of the disclosure accompanies drawings, which are incorporated in and constitute a part of this specification, and illustrate embodiments of the disclosure, but the disclosure is not limited to the embodiments. In addition, the following embodiments can be properly integrated to complete another embodiment.

References to "one embodiment," "an embodiment," "other embodiments," "some embodiments," "another embodiment," etc. indicate that the embodiment(s) of the disclosure so described may include a particular feature, structure, or characteristic, but not every embodiment necessarily includes the particular feature, structure, or characteristic. Further, repeated use of the phrase "in the embodiment" or "in some embodiments" does not necessarily refer to the same embodiment, although it may.

Unless specifically stated otherwise, as apparent from the following discussions, it is appreciated that throughout the specification discussions utilizing terms such as "measuring," "receiving," "calculating," "detecting," "transmitting," or the like, refer to the action and/or processes of a computer or computing system, or similar electronic computing device, state machine and the like that manipulate and/or transform data represented as physical, such as electronic, quantities into other data similarly represented as physical quantities.

In addition, unless specifically stated otherwise, as apparent from claims and detailed description, it is appreciated that throughout the specification the quantity of components is single. If the quantity of the labeled component is one, the quantifier is explained to include one unit or at least one unit. If the quantity of the labeled component is a plurality, the quantifier is explained to include at least two units.

FIG. 1 illustrates an exploded view of some components of a biochemical sensing strip according to some embodiments of the present disclosure. A sensor strip 100, such as the biochemical sensor strip, includes a substrate 1, electrode systems 10, an insulation layer 2, a reactive layer 4, and a covering layer 3.

The substrate 1 includes the electrode systems 10 on top of the substrate 1. The electrode system 10 includes a first electrode set 11 and a second electrode set 12. The first electrode set 11 is disposed outside of the second electrode set 12. The first electrode set 11 is disposed next to the second electrode set 12. For example, the first electrode set 11 is lined against the second electrode set 12. The first electrode set 11 is closer to a sampling port 21 than the second electrode set 12. An aperture of the insulation layer 2 is the sampling port 21.

A recess 7 is between the first electrode set 11 and the second electrode set 12. The first electrode set 11 is disposed between the sampling port 21 and the recess 7. The reactive layer 4 includes a first reactive region 25 and a second reactive region 27. The recess 7 is between the first reactive region 25 and the second reactive region 27. The first reactive region 25 includes a portion of the first electrode set 11. The second reactive region 27 includes a portion of the second electrode set 12.

The first reactive region 25 and the second reactive region 27 are in a reactive zone 20. The reactive zone 20 is in an opening of the insulation layer 2. The opening includes an aperture. The aperture serves as the sampling port 21. In some embodiments, the sampling port 21 is an entrance of the sample, such as blood, coming into the sensor strip 100. The reactive zone 20 includes a width W20 and a side length L20.

The insulation layer 2 includes a backside S23 at a back of the reactive zone 20. The backside S23 includes the width W20. The insulation layer 2 includes two lateral sides S20 at either side of the reactive zone 20. The lateral side S20 can be a length side of the reactive zone 20. The lateral side S20 is hydrophilic. The lateral side S20 includes a length L20 from the sampling port 21 to the backside S23.

The insulation layer 2 is between the substrate 1 and the covering layer 3. The covering layer 3 includes a hole 30. The hole 30 can be a vent opening on top of the reactive zone 20. In some embodiments, the hole 30 is over the second reactive region 27. The second electrode set 12 can be disposed between the recess 7 and the hole 30. The hole 30 is disposed between the backside S23 and the second electrode set 12.

In some embodiments, the substrate 1 is a thin-layered plate with a flat surface and electric insulating properties. More preferably, an insulating substrate is selected, but not limited, from a group consisting of polyvinyl chloride (PVC) plates, fiber glass (FR-4) plates, polyester sulphone, bakelite plates, polyester (PET) plates, polycarbonate (PC) plates, glass plates and ceramic plates (CEM-1).

In some embodiments, the electrode system 10 includes at least two metal electrode sets that are isolated and disconnected from each other. The electrode set can include carbon paste, gold paste, silver paste, mixed carbon-silver paste, evaporated graphite, copper paste, a combination thereof (e.g., screen printing of silver paste initially, followed by printing of carbon paste), or any conductive paste material that is suitable for screen printing and can be dried at below 80° C.

In some embodiments, the insulation layer 2 is a thin layer formed by a material with electric insulating properties. The insulation layer 2 can includes material such as PVC insulation tape, PET insulation tape, thermal curing adhesive and ultraviolet photo-curable adhesive.

Figure 2A:
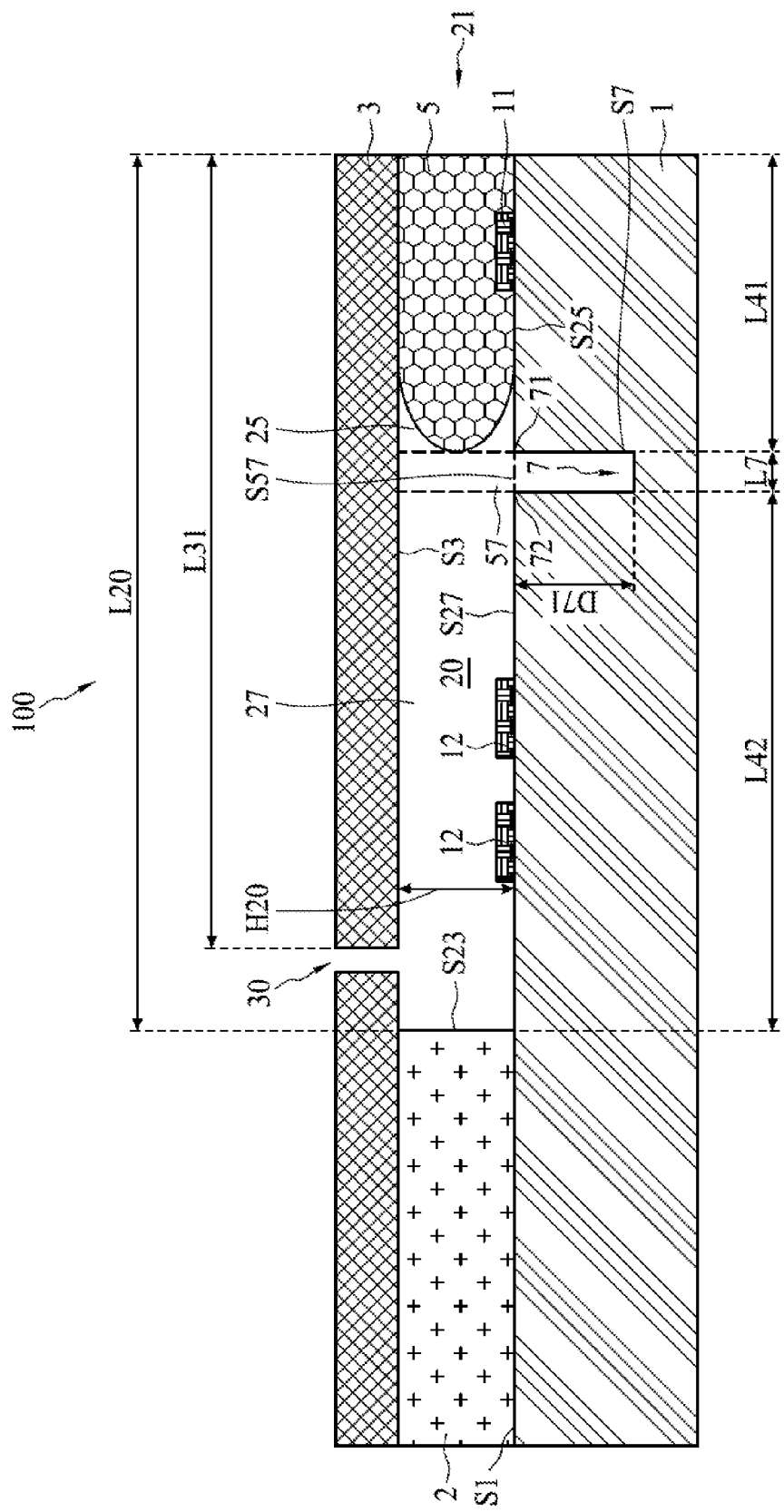

FIG. 2A to 2F are cross-sectional views of the sensor strip 100 according to some embodiments of the present disclosure. As illustrated in FIG. 2A, in some embodiments, at least two electrodes (first electrode set 11 and second electrode set 12) are disposed on top of the substrate 1. The insulation layer 2 is disposed on the substrate 1. The covering layer 3 is disposed on the insulation layer 2. The covering layer 3, the insulation layer 2, and the substrate 1 together form a reactive zone 20 and a sampling port 21 such that a top, a bottom, and three side walls (except the sampling port 21) of the reactive zone 20 are surrounded by the covering layer 3, the substrate 1, and the insulation layer 2 to form a tubular space. When a sample 5 enters the tubular space, a sample adhesion within the tubular space is greater than cohesion of the sample 5 such that the sample 5 continues to advance. Additionally, the covering layer 3 includes a hole 30 to strengthen a capillary action and to exhaust gas in the reactive zone 20. According to some embodiments of the present disclosure, the substrate 1 includes a recess 7 between the first electrode set 11 and the second electrode set 12. The recess 7 includes a hydrophobic material to prevent the sample 5 from entering the recess 7.

The substrate 1 includes a first surface S25 and a second surface S27. The recess 7 is between the first surface S25 and the second surface S27. A third surface (inner surface) S7 in the recess 7 is hydrophobic. In some embodiments, the recess 7 can be a gas containing space to hold gas, such as air, inside the recess 7. The inner surface S7 surrounding the recess 7 is bordered with the first surface S25 and the second surface S27. The first electrode set 11 is disposed on top of the first surface S25. The second electrode set 12 is disposed on top of the second surface S27. The covering layer 3 includes a covering surface S3 facing the substrate 1. The covering surface S3 is hydrophilic and is over the first surface S25, the second surface S27, and the recess 7.

The first reactive region 25 is over the first surface S25 and under the covering surface S3. The second reactive region 27 is over the second surface S27 and under the covering surface S3. The first surface S25 includes a first edge 71 bordering with the recess 7. The second surface S27 includes a second edge 72 bordering with the recess 7. The second edge 72 is opposite to the first edge 71. The first reactive region 25 extends from the sampling port 21 to the first edge 71. The second reactive region 27 extends from the second edge 72 to the backside S23. In some embodiments, the second reactive region 27 extends from the second edge 72 to the hole 30. The first edge 71 is distanced from the second edge 72 by a recess length L7. The length L7 is measured in a direction parallel to the first surface S25 or the second surface S27. The direction is from the sampling port 21 toward the backside S23.

The first surface S25 in the first reactive region 25 includes a length L41 extending from the sampling port 21 to the first edge 71. The second surface S27 in the second reactive region 27 includes a length L42 extending from the second edge 72 to the backside S23.

The recess 7 includes a depth D71 from the first edge 71 or the second edge 72 to a bottom of the inner surface S7. The recess 7 includes a top surface S57. The substrate 1 includes a surface S1 at a top of the substrate 1. The surface S1 is substantially coplanar with the first surface S25, the second surface S27, or the top surface S57. In some embodiments, at least one of the first surface S25 and the second surface S27 is hydrophilic. The top surface S57 is from the first edge 71 to the second edge 72. The top surface S57 includes the length L7. A region 57 is over the top surface S57 and under the covering surface S3. The region 57 is over the recess 7 and between the first reactive region 25 and the second reactive region 27. The first reactive region 25 and the second reactive region 27 are disconnected and separated by the region 57. The region 57 includes a region volume vertically over the recess 7 such that interfaces between the region 57 and the first reactive region 25 or between the region 57 and the second reactive region 27 are substantially vertical. A recess volume inside the recess 7 is surrounded by the inner surface S7 and the top surface S57. The region volume is vertically over the recess volume. In some embodiments, a ratio between the region volume and the recess volume is substantially from around 1 to around 3. The reactive zone 20 includes the first reactive region 25, the region 57, and the second reactive region 27.

The surface S1 is distanced from the covering surface S3 by a height H20. The backside S23 includes the height H20. The covering layer 3 is disposed over the reactive zone 20. The hole 30 is disposed away from the sampling port 21 by a length L31. The length L31 can be a covering length over the reactive zone 20. The reactive zone 20 includes a length L20 from the sampling port 21 to the backside S23. In some embodiments, the length L31 is smaller than the length L20. In some embodiments, a ratio between the length L20 and the length L7 is from around 5 to 10. The sample 5 stops flowing beyond the hole 30. The sample 5 fills the second reactive region 27 of the reactive zone 20 just before the hole 30. In some other embodiments, a ratio between the length L31 and the length L7 is from around 5 to around 10.

Figure 2B:
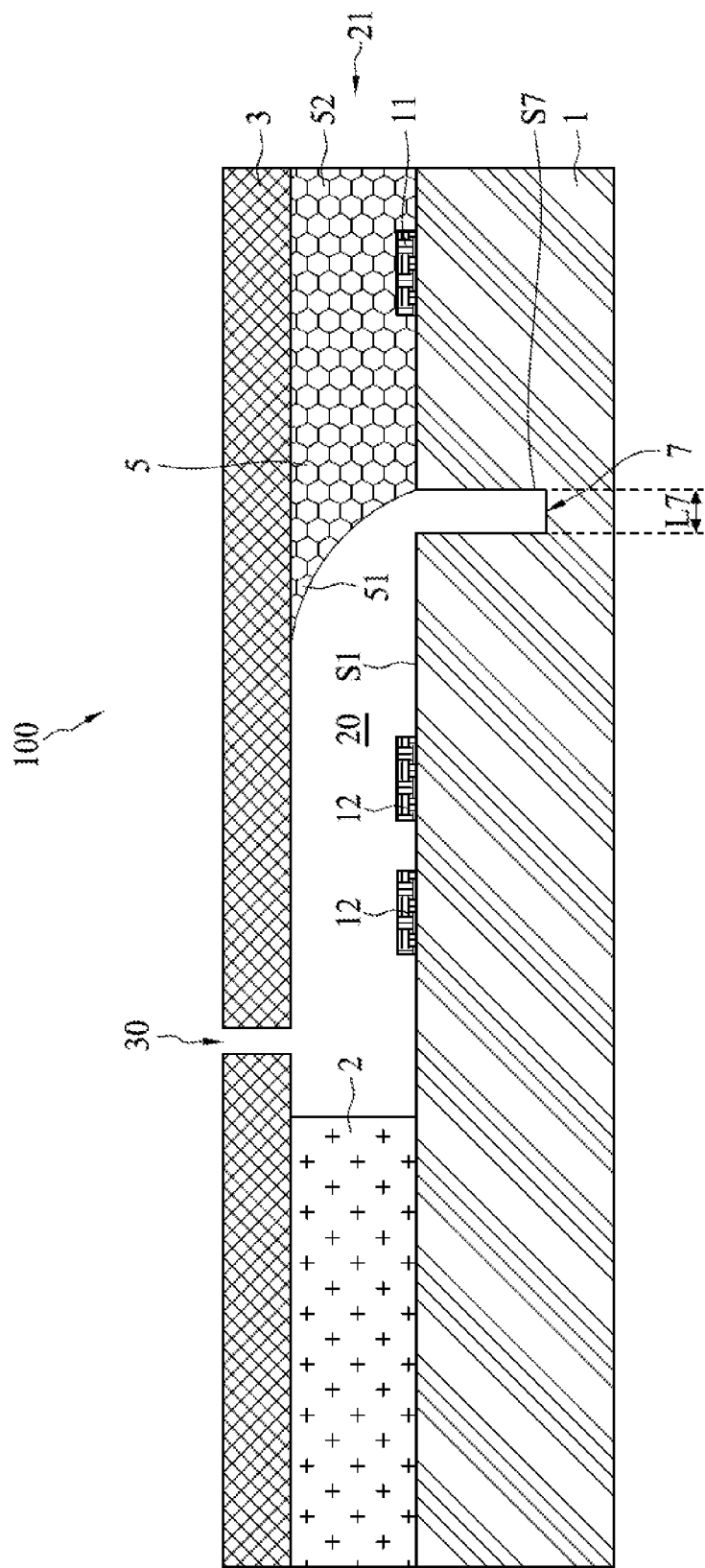

As illustrated in FIG. 2B, the sample 5 loses an adhesive force meant to adhere to the substrate 1 at a junction, such as the first edge 71 of the recess 7. This is due to the capillary effect after the sample 5 enters into the reactive zone 20, considering at least one recess 7 is disposed on the substrate 1 and the recess 7 includes the hydrophobic material inside the recess 7. The sample 5 stays stagnant at the junction. However, a front portion 51 of the sample 5 near the covering layer 3 still includes the adhesive force with the covering layer 3 and continues in a direction toward the hole 30 in the reactive zone 20. Because the sample 5 includes a mutual attraction force (cohesion), a rear portion 52 of the sample 5 crosses through the recess 7 by the cohesion with the front portion 51 of the sample 5 and continues in a direction toward the hole 30.

The sample 5 is outside of the recess 7. The sample 5 is over the recess 7. The sample 5 is in contact with the covering surface S3 of the covering layer 3. The rear portion 52 is in contact with the first surface S25. The front portion 51 of the sample 5 is over the second surface S27.

Figure 2C:
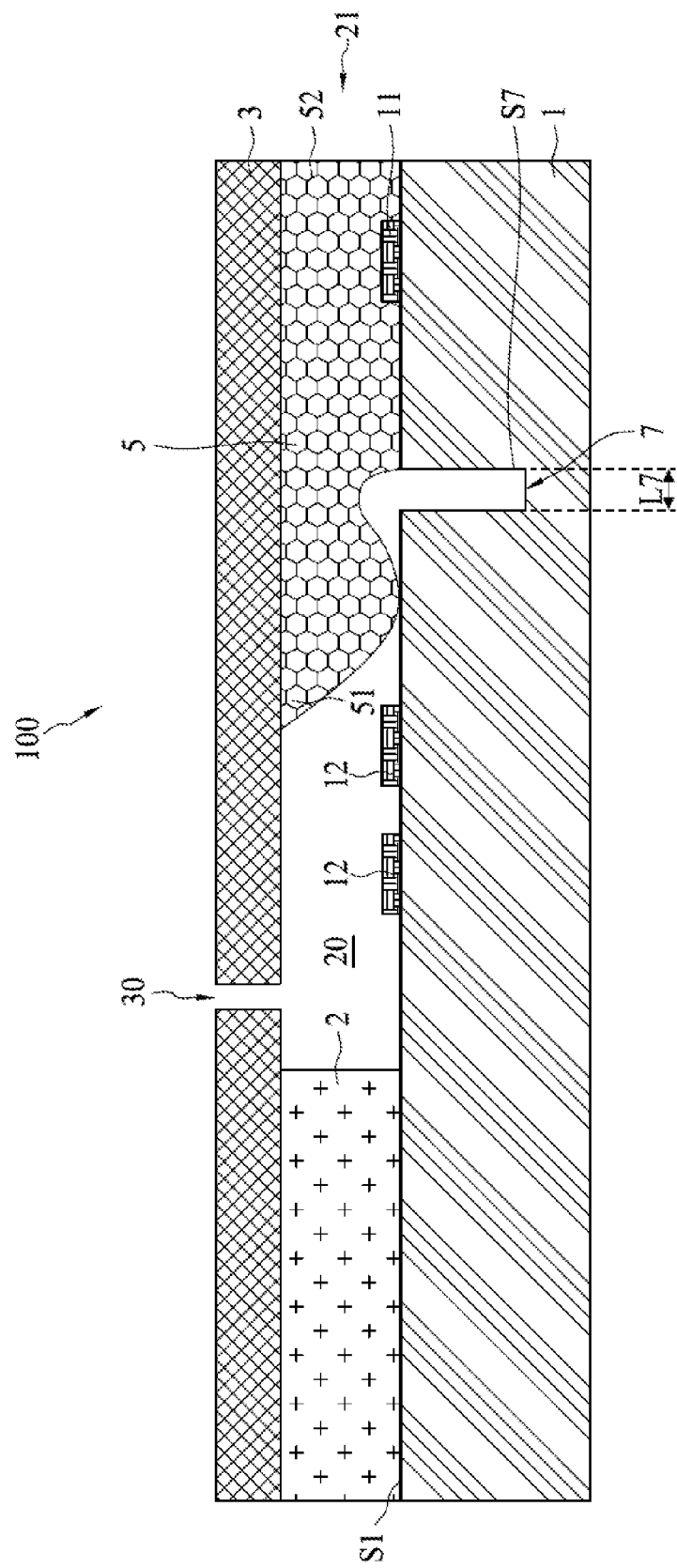

As illustrated in FIG. 2C, the sample 5 stays stagnant on the substrate 1 due to the recess 7. However, because the sample 5 still includes the cohesion effect and the adhesion force with the covering layer 3, the sample 5 crosses through the recess 7 and advances in a direction toward the hole 30. The front portion 51 crossing through the recess 7 loses the adhesion force of the substrate 1 to the sample 5 and slows down an advancing speed. The front portion 51 void of a support from the substrate 1 is affected by the force of gravity. The cohesion of the rear portion 52 to the front portion 51 remains unabated such that the sample 5, resulting from avoiding the hydrophobic materials in the recess 7, continues to thicken until the front portion 51 once again comes into contact with the substrate 1.

The force of gravity pulls the sample 5 downward, and the adhesion force pulls the sample 5 upward. As the sample 5 thickens, a weight of the front portion 51 increases such that the force of gravity pulls the front portion 51 toward the substrate 1 until the sample 5 touches the second surface S27. In some embodiments, the sample 5 is above the recess 7 by the cohesion force within the sample 5 and the adhesion force from the covering layer 3 over the recess 7.

Figure 2D:
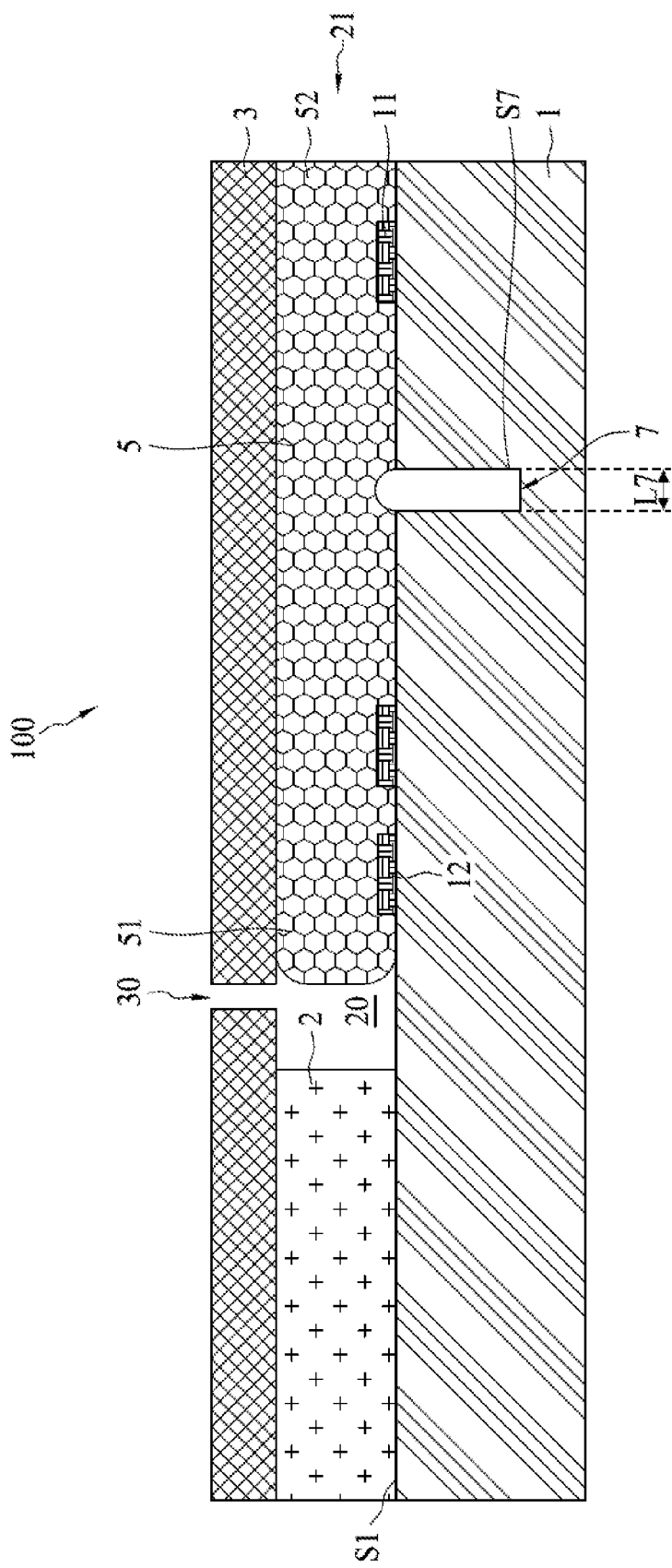

As illustrated in FIG. 2D, after the sample 5 avoids the recess 7, an overall capillary force of the sample 5 restores back to a condition prior to contact with the recess 7. The sample 5 quickly advances toward the hole 30 until a balance is reached between the capillary effect and an atmospheric pressure. The sample 5 over the recess 7 is affected by a repelling force from the hydrophobic material, the adhesion of the covering layer 3, the cohesion of the sample 5, and the gravitational force in such a manner that the sample 5 surrounds air in the recess 7 like a wave.

Figure 2E:
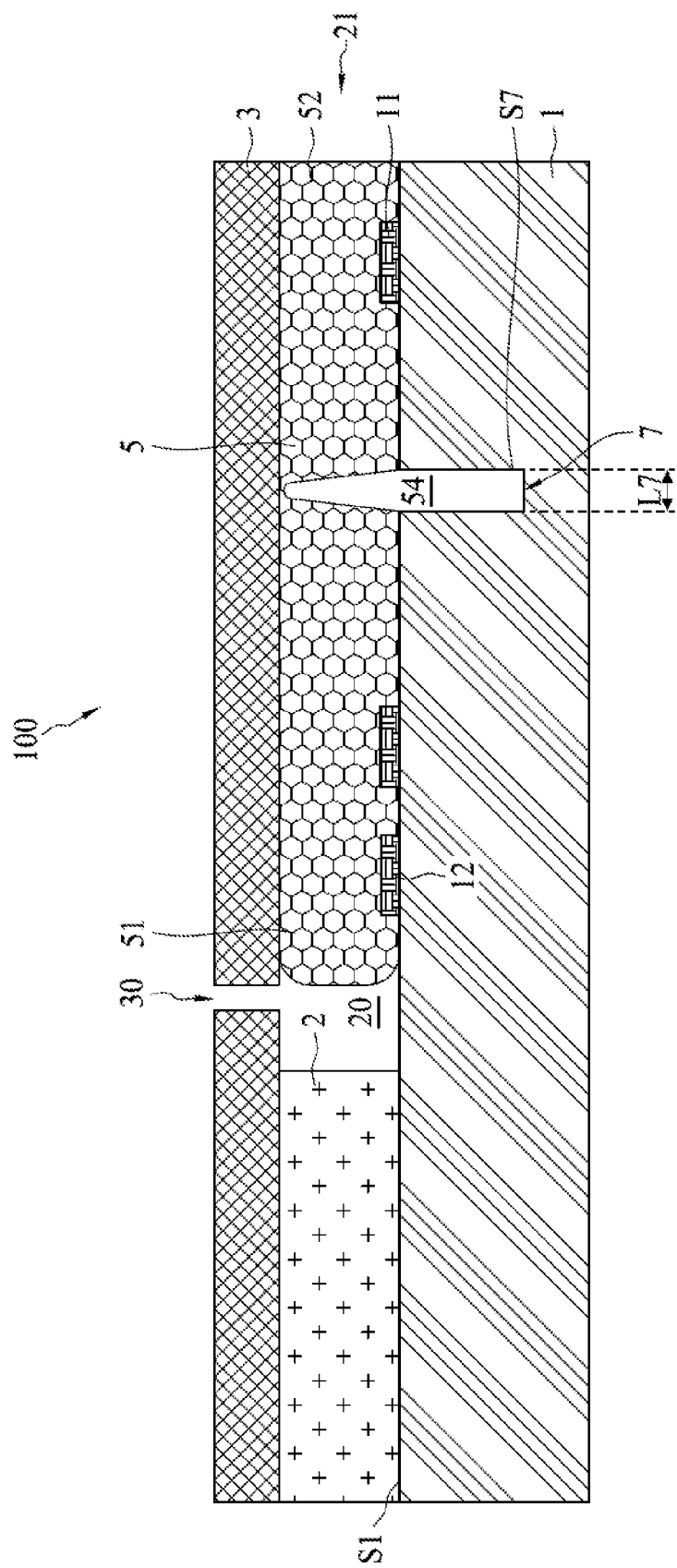

As illustrated in FIG. 2E, the recess 7 includes the hydrophobic material inside to prevent the sample 5 from flowing into the recess 7. In addition, when the capillary effect and the atmospheric pressure are at equilibrium and a hydrophilic property of the substrate 1 is better than the recess 7, the hydrophobic material produces a force pushing the sample 5 toward the sampling port 21 and the hole 30. The sample 5 hanging vertically over the recess 7 by the adhesion of the covering layer 3 is in contact with an air bubble 54. An air density is lower than a density of the sample 5. The air bubble 54 rises until the air bubble 54 is in contact with the covering layer 3. The sample 5 hanging vertically over the recess 7 is pushed toward the hole 30 and the sampling port 21. The sample 5 forms two non-interactive reactive regions such as the first reactive region 25 and the second reactive region 27 divided by the recess 7.

In some embodiments, the sample 5 in the reactive zone 20 including a greater length L20 or a greater length L31 can be separated by the air bubble 54 including a greater volume. The air bubble 54 including a greater volume can be formed by a greater length L7. At equilibrium, the greater length L20 can generate more adhesion force with the sample 5 such that the sample 5 may be harder to move. The air bubble 54 including a greater volume can generate more repelling force to move the sample 5 toward the hole 30 and the sampling port 21.

The recess 7 is between the first reactive region 25 and a second reactive region 27 such that the sample 5 in the first reactive region 25 is disconnected from the sample 5 in the second reactive region 27. In some embodiments, electric currents within the sample 5 in the first reactive region 25 are separated from electric currents within the sample 5 in the second reactive region 27.

Figure 2F:
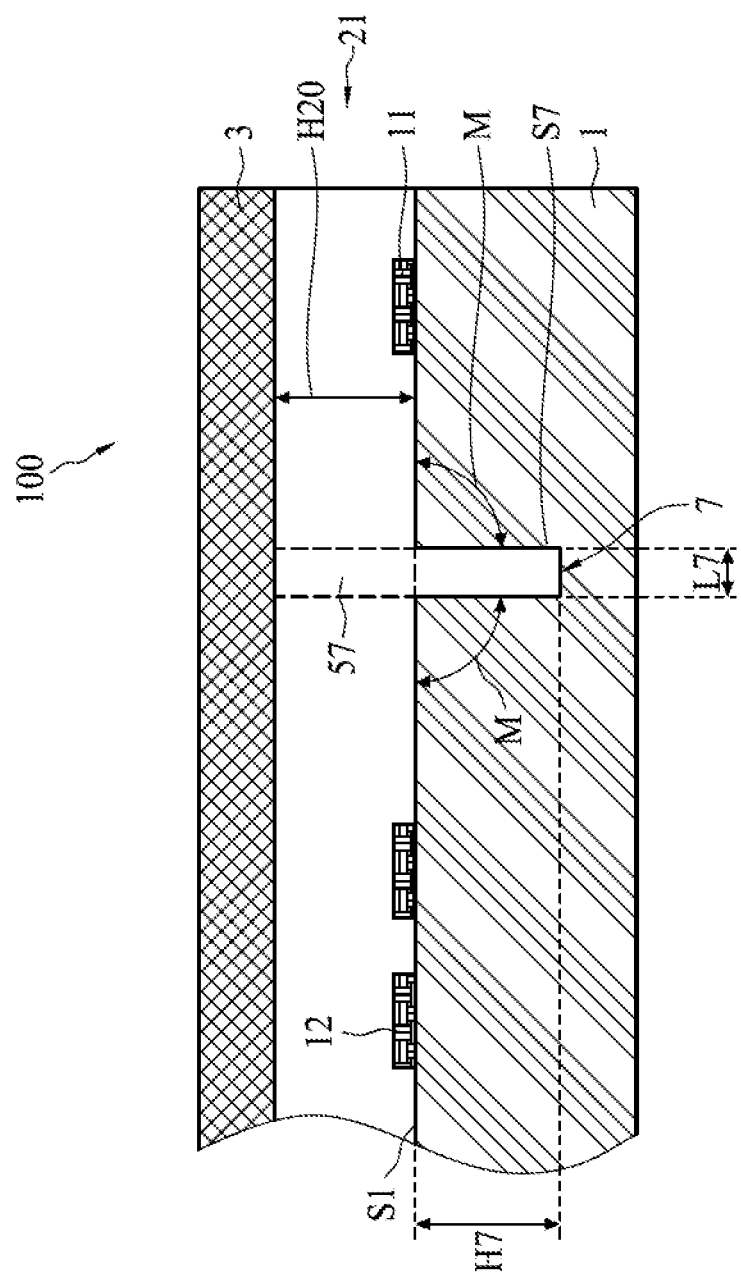

As illustrated in FIG. 2F, the recess 7 includes a length L7. When the length L7 of the recess 7 is too long, the sample 5 stops at the recess 7 and is unable to reach the second electrode set 12. Cohesion forces of the sample 5 are in opposite direction with an adhesion force and the gravitational force. The sample 5 stops at a crossing region as the cohesion force of the sample 5 and the adhesion force are in balance with the gravitational force. A force F of the sample 5 can be calculated as follows:

$$F = \frac{1}{2}abw\rho g$$

where "a" is the length L7 of the crossing region, "b" is a height H20 of the reactive zone 20, "w" is a width W20 of the reactive zone 20 in FIG. 1, "ρ" is a density of the sample 5 in liquid form, and "g" is standard gravity (9.8 m/s$^2$).

In general, the length L7 can be used to control the strength of the gravitational force exerted on the sample 5. As the length L7 becomes smaller, the sample 5 becomes easier to cross the recess 7. A recess volume within the recess 7 is not limited. The recess volume may be sufficient to isolate the first reactive region 25 and the second reactive region 27. A region 57 is the cross region exposed over the recess 7. The region 57 is vertically over the recess 7. The region 57 is a portion of the reactive zone 20. The region 57 is above a surface S1 of the substrate 1 and under the covering layer 3. The region 57 includes a region volume. In some embodiments, the region volume can be greater than the recess volume. In some other embodiments, the region volume is substantially equal to the recess volume. In one embodiment, the recess volume is greater than ⅓ of the region volume.

A ratio between the recess volume and the region volume is proximately smaller than 3. The width W20 is illustrated in a plane view in FIG. 3A. The width W20 is orthogonal to the height H20 and the length L7.

The recess 7 includes a hydrophobic material inside the recess 7. In some embodiments, the recess surface S7 is made of hydrophobic material.

The hydrophobic material can be any suitable material such as alkanes material, oil materials, resin-based material, ink-like material, silicone oil-based material, or nanoscale hydrophobic materials. A preferable hydrophobic material can be polydimethylsiloxane polymers, such as dimethyl polysiloxane and/or other dialkyl polysiloxane, methylphenyl polysiloxane, fluorinated dialkyl polysiloxane, polyorganosiloxane siloxane, and the like. A degree of a contact corner M is between the surface S1 of the substrate 1 and a lateral surface of the recess surface S7. In some other embodiments, strength of the hydrophilic force with the substrate 1 can be increased such that the contact corner M reaches a suitable effect from the hydrophobic material. The degree of the contact corner M can be from around 50 degree to around 180 degree. In some other embodiments, the degree of the contact corner M can be from around 80 degree to around 150 degree.

FIGS. 3A to 3H are plane views of some embodiments of the biochemical sensing strip. In some embodiments, the recess 7 includes a variety of shapes. The recess 7 includes any suitable shapes, such as polygon. The suitable shapes can be square, rectangular, circular, elliptical, triangular, or other shapes.

Figure 3A:
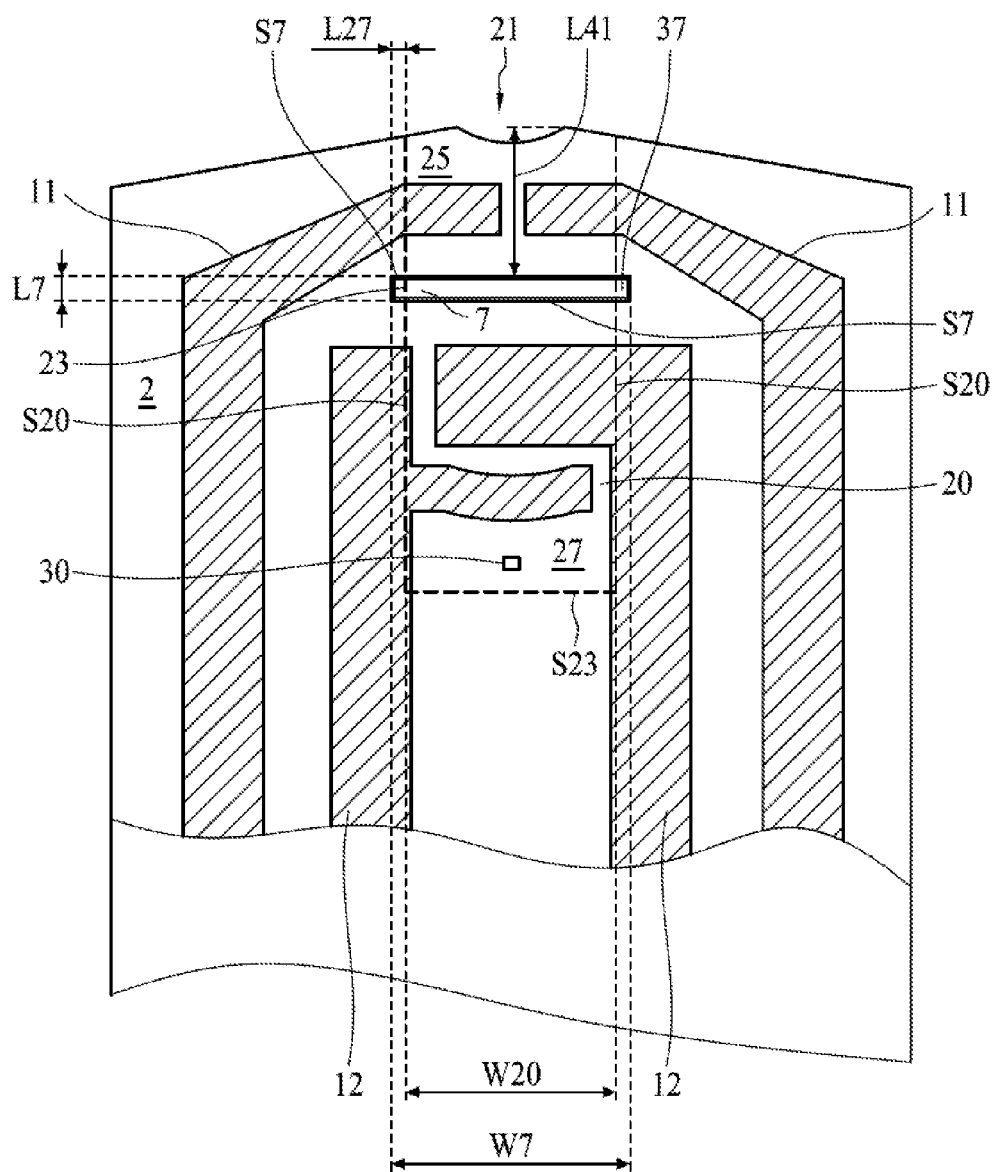

As illustrated in FIG. 3A, the recess 7 is parallel with the sampling port 21 in a horizontal direction. The recess 7 is between the first reactive region 25 and the second reactive region 27. By disposing the recess 7, the sample 5 in the first reactive region 25 and the second reactive region 27 are isolated.

The insulation layer 2 is disposed between the covering layer 3 and the substrate 1. In some embodiments, the insulation layer 2 includes the opening in a rectangular shape. The insulation layer 2 includes the two lateral sides S20 and the backside S23. The opening is between the two lateral sides S20. The opening can contain the sample 5 to serve as the reactive zone 20. The recess 7 is under the insulation layer 2 at the two lateral sides S20. The recess 7 extends beyond the lateral side S20 by a length L27. The recess 7 includes a recess width W7. The recess width W7 is greater than the width W20 of the reactive zone 20 by the length L27. An additional portion 37 of the recess 7 beyond the lateral side S20 includes the length L27. The recess 7 extends beyond the lateral side S20 such that the insulation layer 2 is over the additional portion 37. The additional portion 37 includes an additional volume bounded by the recess surface S7 and a bottom of the insulation layer 2.

The additional portion 37 of the recess 7 extending beyond the lateral side S20 includes additional volume so as to provide additional gas to the air bubble 54 near the lateral side S20. In one embodiment, the lateral side S20 over the recess 7 includes a hydrophilic surface. The sample 5 near the lateral side S20 is attracted to the covering surface S3 and the lateral side S20 by the adhesion forces in an upward direction and a lateral direction. The additional gas in the recess 7 near the lateral side S20 can increase a volume of the air bubble 54 near the lateral side S20. The air bubble 54, including an increased volume near the lateral side S20, can push the sample 5 toward either side of the recess 7. A corner 23 is between the covering surface S3 and the lateral side S20. The increased air bubble 54 can separate the sample 5 at a top near the covering surface S3 and the lateral side S20 with additional forces such that the air bubble 54 near the corner 23 can fully separate and disconnect the sample 5 such that the sample 5 from the first reactive region 25 and from the second reactive region 27 are isolated.

The recess 7 is distanced from the sampling port 21 by a length L41. The reactive zone 20 is illustrated in a dash line. The reactive zone 20 is surrounded by the backside S23, two lateral sides S20, and the sampling port 21. The sampling port 21 is opposite to the backside S23. In some embodiments, the hole 30 is disposed in the second reactive region 27 near the backside S23. The first electrode set 11 is partially within the first reactive region 25. The second electrode set 12 is partially within the second reactive region 27.

Figure 3B:
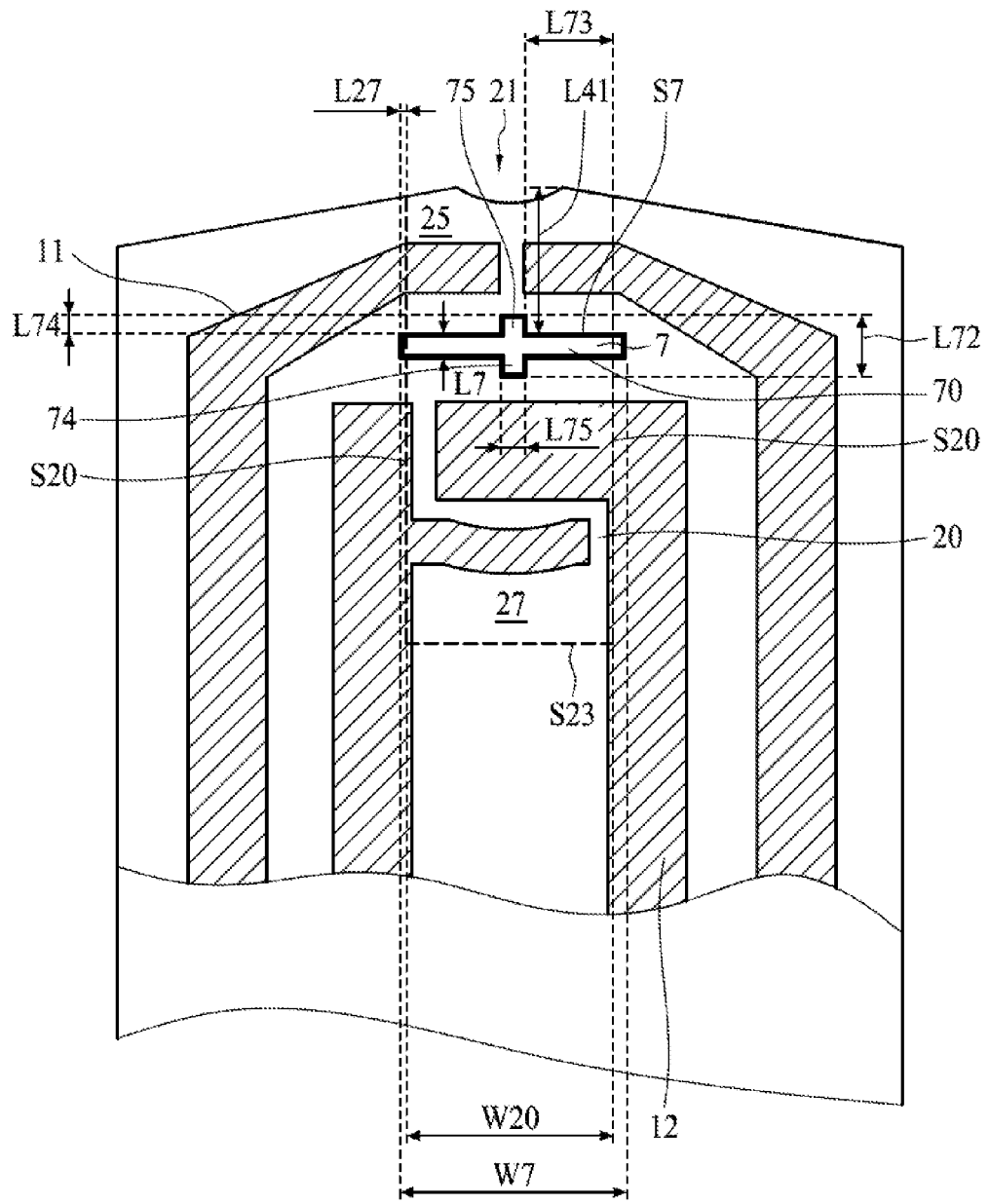

In FIG. 3B, the recess 7 includes a cross configuration. Depending on other measurements or manufacturing factors, when the hydrophilic force is weak in capillary walls, the sample 5 entering into the reactive zone 20 produces friction with the capillary walls such that a portion of the sample 5 not in contact with the capillary wall flows faster than a portion of the sample 5 in contact with the capillary walls. Disposing a short portion 75 of the recess 7 away from the capillary walls allows flow rates of the sample 5 near the short portion 75 and a long portion similar to the recess 7 to be kept uniform. A non-uniform flow rate of the sample 5 is prevented to avoid a reduction of forces for crossing the recess 7.

The capillary walls include a surface S1 of the substrate 1, three side walls of the insulation layer 2, and a covering surface S3 of the covering layer 3. The three side walls of the insulation layer 2 are two lateral sides S20 and the backside S23.

The recess 7 includes the length L7 and the recess width W7 parallel to the covering surface S3 of the covering layer 3. The length L7 is orthogonal to the recess width W7. The recess width W7 extends in a direction from one lateral side S20, such as a first side, to another lateral side S20, such as a second side. In some embodiments, the length L7 is variable in the direction along the recess width W7.

FIG. 3B is similar to FIG. 3A, except that in FIG. 3B, the recess 7 includes the short portion 75. The short portion 75 includes a protruding portion 74 extending in a direction parallel with the lateral side S20. The protruding portion 74 includes a length L74 measured from the long portion toward a tip of the protruding portion 74. The length L7 near the lateral side S20 is smaller than the length L7 within the protruding portion 74 by the length L74. The length L7 is measured in a direction parallel with the lateral side S20. The length L7 within the protruding portion 74 is greater than the length L7 under at least one of the lateral side S20 by at least the length L74. The protruding portion 74 is closer to the sampling port 21 than the long portion 70. The length L41 from the sampling port 21 to the recess 7 is variable. The length L41 from the short portion 75 to the sampling port 21 is shorter than the length L41 from the long portion 70 to the sampling port 21 by the length L74. The short portion 75 includes a total length L72. In some embodiments, the protruding portion 74 of the short portion 75 is extended toward the sampling port 21, toward the backside S23, or both toward the sampling port 21 and the backside S23. The protruding portion 74 includes a width W75 measured in a direction orthogonal to the lateral side S20. The protruding portion 74 is distanced from the lateral side S20 by a length L73. In some embodiments, the protruding portion 74 is disposed in a middle of the recess 7 such that the protruding portion 74 is distanced from the two lateral sides S20 equally.

The protruding portion 74 disposed in the middle of the recess 7 can slow the sample 5 flowing near the protruding portion 74 in the first reactive region 25. In some embodiments, a middle portion of the sample 5 is flowing faster near the middle of the reactive zone 20 than a side portion of the sample 5 near the lateral side S20. The middle portion contacts the protruding portion 74 before contacting other portions of the recess 7. The middle portion slows down to a speed closer to the side portion of the sample 5 such that an average speed of the sample 5 is substantially uniform from one lateral side S20 to another lateral side S20.

Figure 3C:
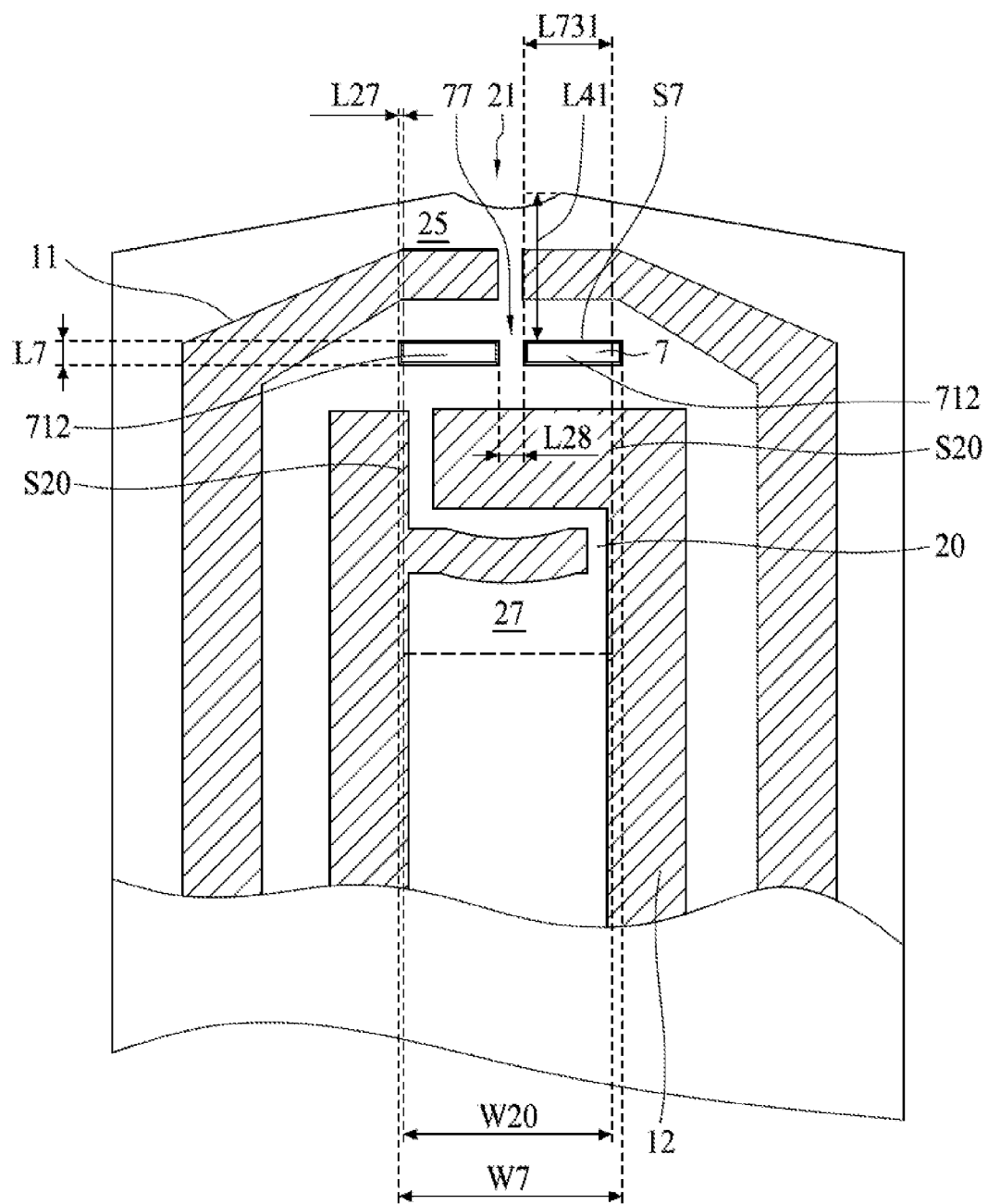

In FIG. 3C, at least two isolated regions 712 of the recess 7 are disconnected. The two isolated regions 712 are disposed such that the sample 5 in the reactive zone 20 can cross through a region 77 without the recess 7. The sample 5 passing through the first reactive region 25 strengthens a capability of the rear portion 52 to cross through the recess 7 by the cohesion force.

FIG. 3C is similar to FIG. 3A, except that in FIG. 3C, the recess 7 is separated into at least two isolated regions 712.

A region 77 can be a passage between the isolated regions 712. The region 77 includes a length L8 from one edge of an isolated region 712 to one edge of another isolated region 712. The region 77 is distanced from the lateral side S20 by a length L731. In some embodiments, the region 77 is disposed in a middle of the recess 7. The region 77 can be a thin region crossing through the recess 7. The region 77 couples between the first surface S25 and the second surface S27.

The region 77 can allow the sample 5 to flow from the first reactive region 25 to the second reactive region 27. Depending on other measurements or manufacturing factors, when the hydrophilic force is weak in capillary walls, the sample 5 entering into the reactive zone 20 flows slowly across the recess 7. In some embodiments, the sample 5 includes a strong cohesion force. The region 77 can enhance a crossing capability of the sample 5. The region 77 allows a slowly flowing sample 5 to pass through the recess 7. By disposing the region 77 between the first reactive region 25 and the second reactive region 27, the flow rates of the sample 5 entering toward the region 77 is greater than the flow rates of the sample 5 in contact with the isolated region 712. The sample 5 entering into the region 77 is a fast portion. The sample 5 coming into contact with the isolated region 712 is a slow portion. With strong cohesion force within the sample 5, the fast portion of the sample 5 can pull the slow portion of the sample 5 crossing through the recess 7.

After the sample 5 crosses over the recess 7, the air bubbles 54 form over the isolated regions 712. The air bubble 54 from one isolated region 712 combines with another air bubble 54 from another isolated region 712 such that a joined air bubble extends over the region 77 from one isolated region 712 to another isolated region 712. The hydrophobic surface in the recess 7 pushes away the sample 5 over the region 77 near the isolated region 712 such that the sample 5 over the region 77 is reduced as the air bubbles 54 combine. The joined air bubble is over the isolated regions 712 and the region 77. The joined air bubble fully separates the sample 5 in the first reactive region 25 and the sample 5 in the second reactive region 27. The joined air bubble extends from one lateral side S20 to another lateral side S20. The joined air bubble over the region 77 extends from the surface S1 of the substrate 1 to the covering surface S3 of the covering layer 3. The joined air bubble extends from the first surface S25 to the second surface S27.

In some embodiments, a smaller length L28 can form the joined air bubble more easily. A longer length L28 can allow the sample 5 to cross through the recess 7 more easily. A suitable length L28 can be determined to form the joined air bubble and allow the sample 5 to cross through the recess 7.

Figure 3D:
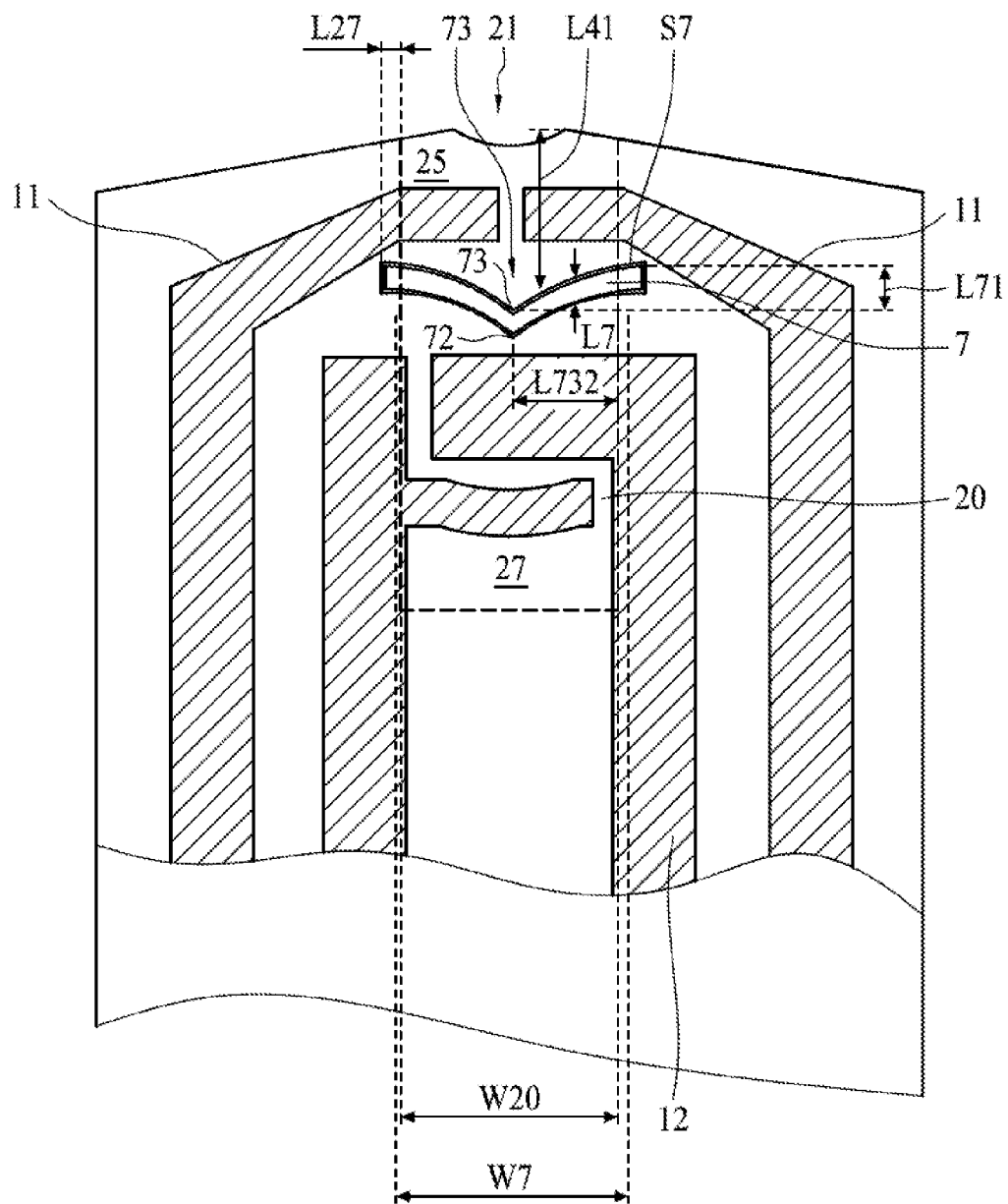
Figure 3E:
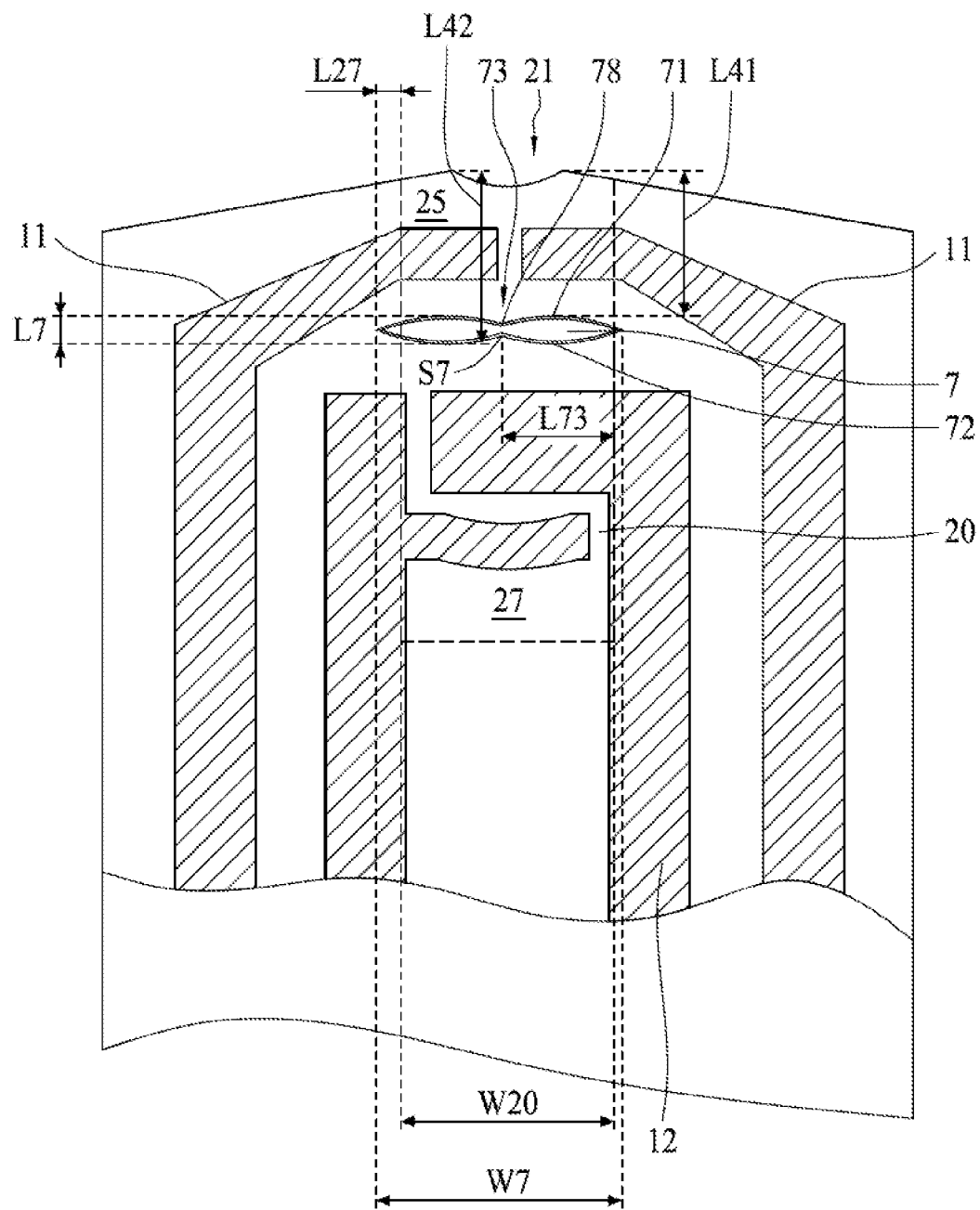
Figure 3F:
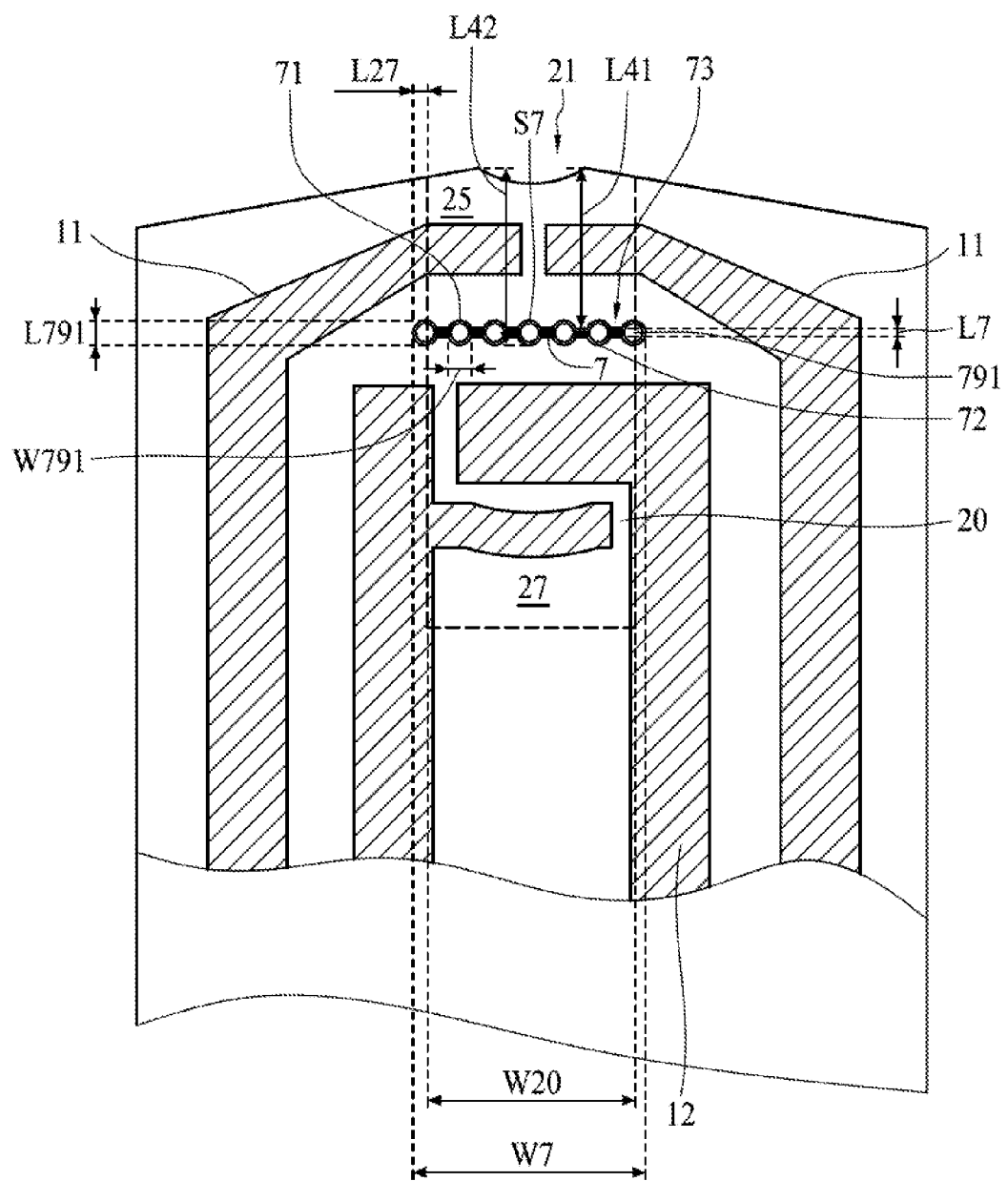

In FIGS. 3D to 3F, using a non-parallel recess 7 lowers a resistance from the recess 7 to the sample 5 at a same level. The non-parallel recess 7 strengthens the capability of the sample 5 to cross through the recess 7.

In FIG. 3D, the first edge 71 of the recess 7 includes at least more than two portions which are non-parallel with each other. The length L41 between the first edge 71 and the sampling port 21 is variable from one lateral side S20 to an opposite lateral side S20. In some embodiments, the length L41 is increasing then decreasing. In some embodiments, a portion of the recess 7 near the lateral side S20 includes the length L41 shorter than the length L41 of other portions of the recess 7. In some embodiments, the first edge 71 is concaved inward and protruding toward the backside S23. In some embodiments, the first edge 71 is bent to form a shape of an arrow. A tip of the arrow points toward the backside S23. The arrow is a protruding portion of the first edge 71.

In some embodiments, the tip of the arrow is distanced from the first edge 71 at the lateral side S20 by a length L71. The tip is distanced from the lateral side S20 by the length L732. In some embodiments, the second edge 72 follows a contour of the first edge 71 such that the length L7 between the first edge 71 and the second edge 72 is substantially constant from one lateral side S20 to an opposite lateral side S20. In some other embodiments, the length L7 is variable along the recess 7. For example, the length L7 near the lateral side S20 is greater than the length L7 near the tip of the arrow.

In some embodiments, the second edge 72 includes a shape of an arrow. An arrow tip of the second edge 72 is offset from the arrow tip of the first edge 71. For example, the arrow tip of the second edge 72 is closer to the lateral side S20 than the arrow tip of the first edge 71 to the lateral side S20.

A concave 73 of the first edge 71 allows the sample 5 to flow from the first reactive region 25 to the second reactive region 27 at different flow rates. Depending on other measurements or manufacturing factors, when the hydrophilic force is weak in capillary walls, the sample 5 entering into the reactive zone 20 flows slowly before touching the recess 7. The concave 73 can enhance the crossing capability of the sample 5. As the sample 5 flows toward the first edge 71 of the recess 7, a portion of the sample 5 touches the first edge 71 before other portions of the sample 5. The portion in contact with the first edge 71 is already hindered by the hydrophobic surface in the recess 7 while another portion continues to flow until touching another portion of the first edge 71. The portion of the sample 5 in contact with the first edge 71 earlier travels a shorter distance of the length L41 than the other portions. By varying the length L41 across the recess 7, or along a direction orthogonal to the lateral side S20, the flow rates of the sample 5 entering toward the tip of the arrow is greater than the flow rates of the sample 5 already in contact with the first edge 71. The sample 5 entering into the concave 73 is a fast portion. The sample 5 already in contact with the first edge 71 is a slow portion. By the cohesion force within the sample 5, the fast portion of the sample 5 can pull the slow portion of the sample 5 crossing through the recess 7. Instead of being completely hindered by the recess 7, as by the recess 7 in FIG. 3A, the slow portion of the sample 5 may move toward the fast portion and toward the tip of the arrow to increase a pressure of the sample 5 near the tip. Increasing the pressure at the tip may help allow the sample 5 to cross over the recess 7.

In some embodiments, in FIG. 3E, the recess 7 includes a concave portion 78 between the lateral sides S20. The length L7 is smaller near the concave portion 78 or the lateral side S20 than near other portions of the recess 7. The first edge 71 of the recess 7 in FIG. 3E includes the concave 73 near the concave portion 78, which is similar to the concave 73 in FIG. 3D. The recess 7 in FIG. 3E further includes a variable length L7 along the recess 7.

The second edge 72 of the recess 7 is non-parallel with the first edge 71. The second edge 72 includes another concave 73 resembling another arrow including another tip pointing toward the sampling port 21 opposite to the tip of the first edge 71. The tip of the first edge 71 and the tip of the second edge 72 are pointing toward each other. The length L7 between the two tips is shorter than the length L7 of some neighboring portions of the recess 7. In some embodiments, the length L41 from the tip of the first edge 71 is substantially equal to the length L41 of the recess 7 under the lateral side S20. A length L42 is from the second edge 72 to the sampling port 21. The length L42 is variable along the recess 7.

The concave 73 of the first edge 71 and an increase of the length L41 near the lateral side S20 allows the sample 5 to flow at different flow rates near the first edge 71. Depending on other measurements or manufacturing factors, when the hydrophilic force is weak at the lateral side S20, the sample 5 in contact with the lateral side S20 flows slowly near the first edge 71. Increasing the length L41 near the lateral side S20 more than the length L41 further away from the lateral side S20 can enhance the crossing capability of the sample 5 similar to the concave 73 of the first edge 71. As the sample 5 flows toward the concave 73 and near the lateral side S20, some portions of the sample 5 touch the first edge 71 later than other portions of the sample 5. The portions in contact with the first edge 71 near the lateral side S20 are hindered by the hydrophobic surface in the recess 7. When the hydrophilic force from the lateral side S20 is weak, the hindrance can be reduced by allowing the portions of the sample 5 to flow further along the length L41 than other portions before touching the first edge 71. By increasing the length L41 near the lateral side S20, the flow rates of the sample 5 near the lateral side S20 are greater than the flow rates of the sample 5 further away from the lateral side S20. Some fast portions enter into the concave 73 and near the lateral sides S20. Other portions of the sample 5 in contact with the first edge 71 earlier are slow portions. By the cohesion force within the sample 5, the fast portions of the sample 5 can pull the slow portions of the sample 5 across the recess 7. Instead of being completely hindered by the recess 7, as by the recess 7 in FIG. 3A, the slow portions of the sample 5 may move toward the fast portions near the concave 73 and the lateral side S20 to increase the pressure of the sample 5 and push the sample 5 across over the recess 7 and toward the second reactive region 27.

The second edge 72 can have the concave 73 and bend toward the sampling port 21 near the lateral side S20 such that the length L7 near the concave 73 and the lateral side S20 is small compared to neighboring portions of the recess 7. In some embodiments, a variation of the length L42 is symmetrical to a variation of the length L41. The variation of the length L42 includes smaller length near the concave 73 and the lateral sides S20 than other portions of the recess 7.

A difference between the length L42 and the length L41 is approximately the length L7. Variation of the length L7 affects the crossing capability of the sample 5. Varying the length L41 and the length L7 along the recess 7 increases the crossing capability of the sample 5.

In some embodiments, the concave 73 is offset from the middle of the recess 7. For example, the concave 73 can be closer to one of the lateral sides S20 than to the other lateral side S20.

In FIG. 3F, in some embodiments, the variation of the length L41 and the length L42 are opposite. For example, in a direction from one lateral side S20 to another lateral side S20, the length L41 increases as the length L42 decreases such that the length L7 is decreasing. Alternatively, the length L41 decreases as the length L42 increases such that the length L7 is increasing.

In FIG. 3F, in some embodiments, a pattern of the variation of the length L41 and the length L42 is repeated along the recess 7. The length L7 is increasing and decreasing repeatedly to form a series of expanded portions 791 of the recess 7 across the recess 7. The expanded portion 791 includes a length L791. In some embodiments, the expanded portion 791 is circular such that a width W791 is substantially equal to the length L791 measuring in a direction parallel with the lateral side S20. In some embodiments, the lateral side S20 is over the expanded portion 791 such that the length L7 under the lateral side S20 is enlarged to the length L791. The series of the expanded portions 791 forms the first edge 71 in a shape similar to a wave. The wave includes crests pointing toward the sampling port 21 and troughs pointing toward the backside S23.

The sample 5 flowing toward the first edge 71 conforms to the wave shape of the first edge 71. The sample 5 includes the slow portion in contact with the crests of the wave shape. The sample 5 includes the fast portion coming into the troughs of the wave shape. The sample 5 contacting the first edge 71 of the recess 7 resembles a shape of a saw tooth. The fast portions bring the slow portions of the sample 5 similar to FIG. 3E.

Instead of including the arrow shape with the tip as in FIG. 3E, in FIG. 3F, the concave 73 includes a flat portion. The length L7 near the flat portion is suitably small to allow the fast portion of the sample 5 to cross through the recess 7. The expanded portion 791 provides a suitably large volume of air to form the air bubble 54 to separate the sample 5.

Figure 3G:
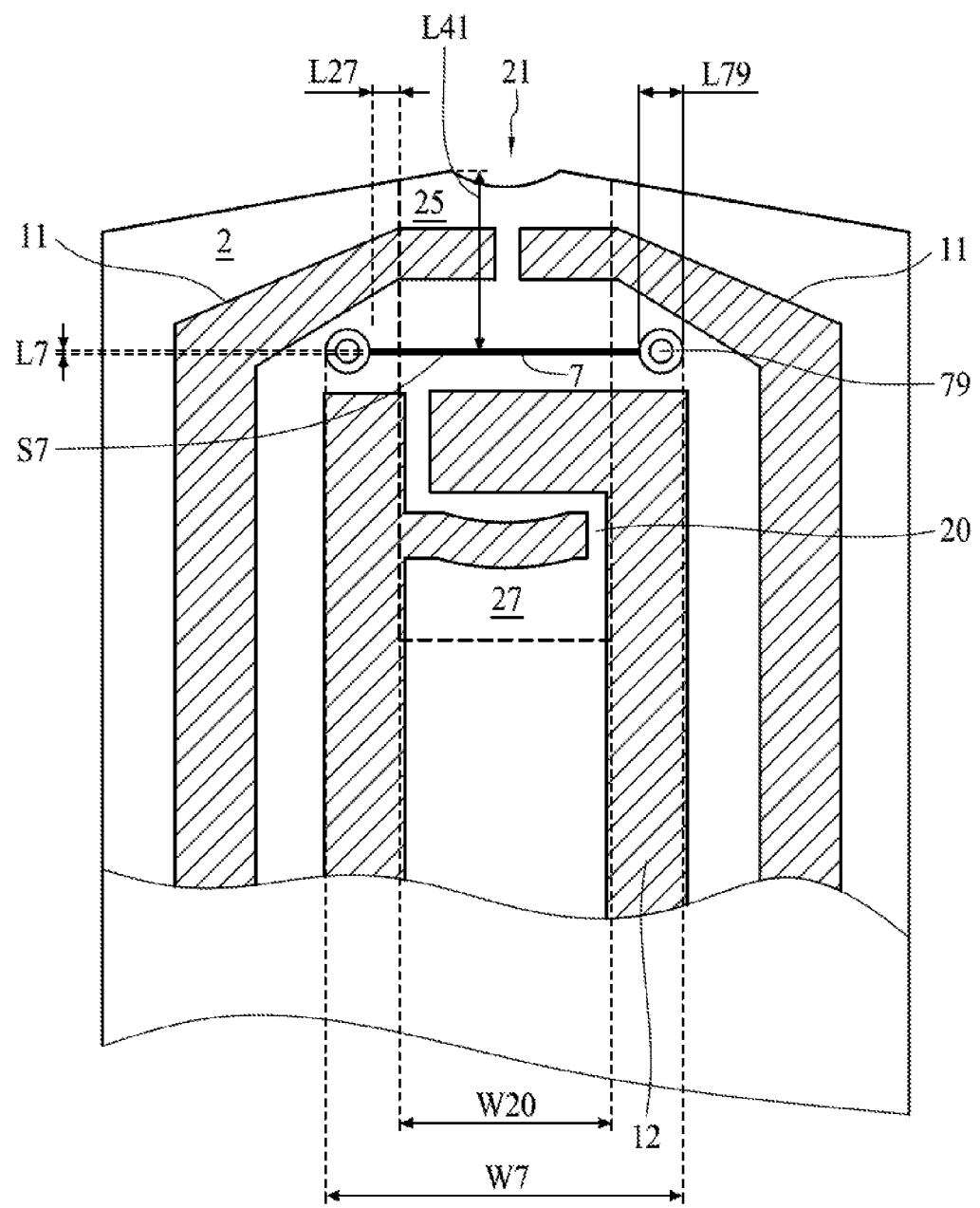

In FIG. 3G, in some embodiments, in addition to the recess 7, at least one gas reservoir 79 is disposed outside of the reactive zone 20. The gas reservoir 79 and the recess 7 are connected such that additional gas can be provided to the recess 7 to separate the first reactive region 25 and the second reactive region 27. Furthermore, the length L7 of the recess 7 can be reduced.

In some embodiments, the gas reservoir 79 is under the insulation layer 2. The gas reservoir 79 includes a length L79. In some embodiments, the length L79 is a diameter of the reservoir 79. The gas reservoir 79 is distanced from the lateral side S20 by a length L27. In some embodiments, the gas reservoir 79 is a portion of the recess 7.

When the length L7 of the recess 7 is too long, the sample 5 stops at the recess 7 and is unable to reach the second electrode set 12. When the length L7 is too short, the recess volume is too small to form the air bubble 54 to fully separate the sample 5. In some embodiments, instead of increasing the length L7, the gas reservoir 79 is added to increase the recess volume. The gas reservoir 79 provides additional volume to the recess volume. The gas reservoir 79 provides additional air to the air bubble 54 to fully separate the sample 5.

Reducing the length L7 reduces the region volume of the region 57. Adding the gas reservoir 79 increases the recess volume. The ratio between the region volume and the recess volume is decreased so as to increase a volume of the air bubble 54. The length L7 is decreased to allow the sample 5 to cross through the recess 7.

Figure 3H:
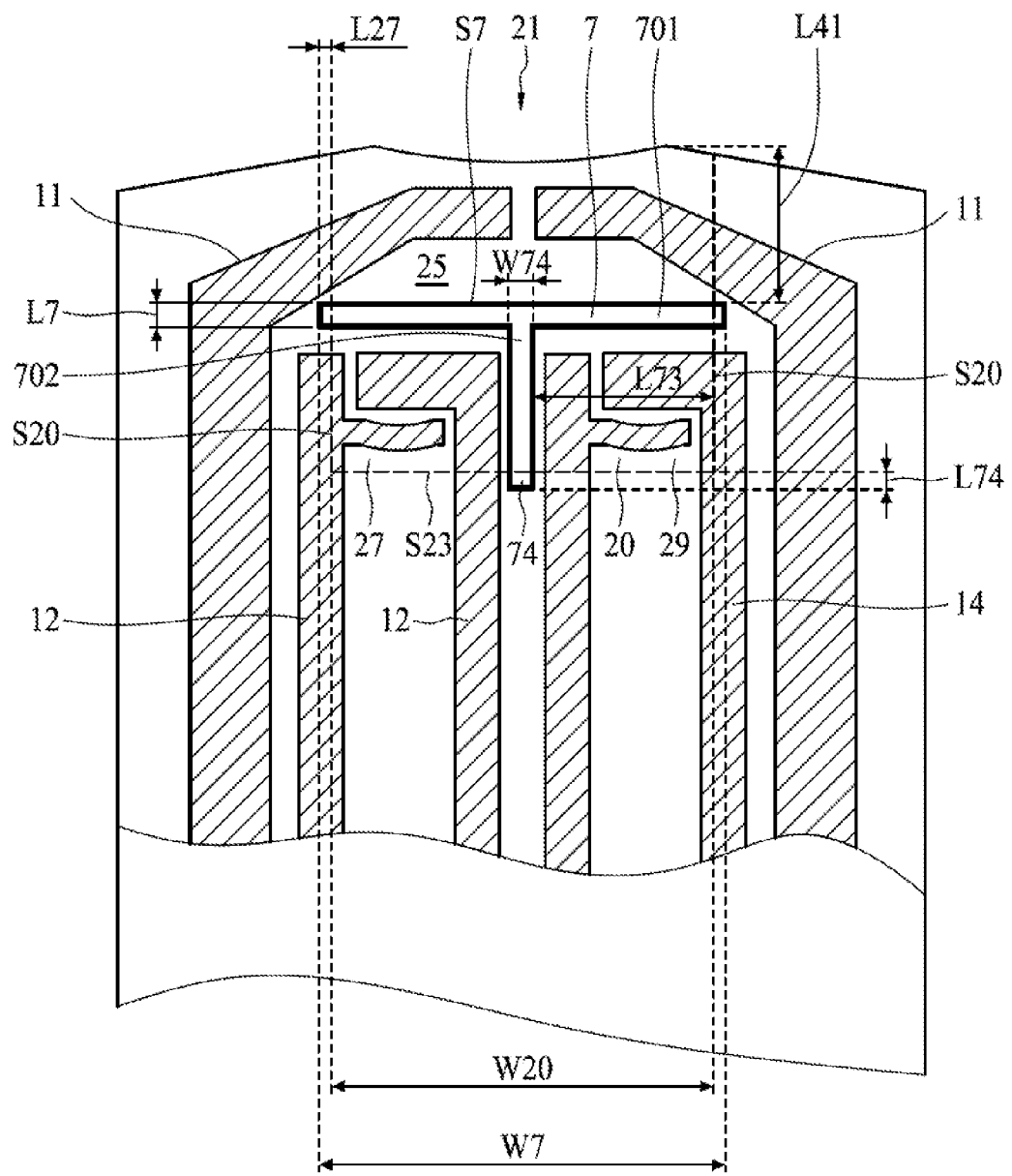

In some embodiments, the sensor strip 100, such as the biochemical sensing strip, can include more than two reactive regions. The sensor strip 100 including multiple reactive zones is illustrated in FIG. 3H. In some embodiments, the recess 7 can include a horizontal portion 701 parallel with the sampling port 21 and a vertical portion 702 orthogonal to the sampling port 21. The sample 5 crosses through the horizontal portion 701 by the adhesion force of the covering layer 3 and the cohesion force in the sample 5. However, because the vertical portion 702 is too long for the sample 5 to cross through, the sample 5 bypasses the vertical portion 702 and flows to the second reactive region 27 and a third reactive region 29. The third reactive region 29 is formed.

In some embodiments, the first reactive region 25, the second reactive region 27, and the third reactive region 29 are isolated by the recess 7. The recess 7 includes the protruding portion 74 of the vertical portion 702 extending to separate the reactive zone 20 into different reactive regions such as the first reactive region 25, the second reactive region 27, and the third reactive region 29. The protruding portion 74 extends to the capillary walls enclosing the reactive zone 20.

The third reactive region 29 includes the third electrode set 14. In some embodiments, the third electrode set 14 is similar to the second electrode set 12. In some embodiments, the third reactive region 29 is parallel to the second reactive region 27. The horizontal portion 701 extends from one of the lateral sides S20 to another lateral side S20. The second reactive region 27 is enclosed by one of the lateral sides S20, the backside S23, and the vertical portion 702. The third reactive region 29 is enclosed by another lateral side S20, the backside S23, and the vertical portion 702. The horizontal portion 701 is similar to the recess 7 in FIG. 3A. The vertical portion 702 extends from the horizontal portion 701 to the backside S23. The vertical portion 702 extends over the backside S23 by a length L25. The vertical portion 702 includes a width W74.

The sample 5 crosses through the horizontal portion 701 to enter into the second reactive region 27 and the third reactive region 29. The vertical portion 702 of the recess 7 includes the hydrophobic surface to separate the sample 5 between the second reactive region 27 and the third reactive region 29. In some embodiments, the width W74 of the vertical portion 702 is similar to the length L7 in the horizontal portion 701. The width W74 is in a suitable range to form the air bubble 54 over the vertical portion 702 to separate the sample 5 between the second reactive region 27 and the third reactive region 29. The air bubble 54 is over the horizontal portion 701 and over the vertical portion 702.

In some embodiments, the vertical portion 702 is in a middle of the horizontal portion 701. In some other embodiments, the vertical portion 702 is disposed away from the middle of the horizontal portion 701. For example, the vertical portion 702 is closer to one of the lateral sides S20 than the other lateral side S20.

A portion of the vertical portion 702 extends over the backside S23 similar to portions of the horizontal portion 701 extending over the lateral sides S20. The second edge 72 includes the protruding portion 74 extending beyond the backside S23. The air bubble 54 over the vertical portion 702 near the backside S23 includes the air from the portion beyond the backside S23.

The embodiments in the present disclosure can be properly integrated to complete some other embodiments. Depending on other measurements or manufacturing factors, in some embodiments, different features of the embodiments such as the short portion 75 in FIG. 3B, the region 77 in FIG. 3C, the concave 73 in FIG. 3D, the expanded portion 791 in FIG. 3F, or the gas reservoir 79 in FIG. 3G may be in different combination to form other embodiments. For example, in some embodiments, the recess 7 can include the gas reservoir 79 near at least one end of the recess 7 and the region 77 of the recess 7 disposed between the lateral sides S20. In some other embodiments, the recess 7 includes the vertical portion 702 extending over the backside S23, and at least one of the short portions 75 in the recess 7 is between the vertical portion 702 and the lateral side S20.

FIG. 4A illustrates a reactive diagram 200 of electrical signals using double reactive regions void of the recess. The first reactive region measures hematocrit and the second reactive region measures the blood sugar concentration. The hematocrit is used to correct the blood sugar concentration. There is no recess separating the first reactive region and the second reactive region such that a reactive agent in the second reactive region refluxes back to the first reactive region, resulting in the first reactive region measuring erroneously large signals. An amount of the reactive agent in the second reactive region is outside of a predetermined range, resulting in measuring an unpredictably low electrical signal.

The reactive diagram 200 compares a measured concentration of a sample with an actual concentration of the sample. The reactive diagram 200 illustrates how much the measured concentration deviates from the actual concentration. For example, for the actual concentration of around 170, the measured concentration can be in a range from around 270 to around 100.

In FIG. 4A, the measured concentration is obtain by using the double reactive regions void of the recess. The lower boundary 202 and the upper boundary 201 set the boundary for the deviation of the measured concentration. For example, in FIG. 4A, for the actual concentration of around 150, the measured concentrations are at around 250 and over the upper boundary 201. Some other measured concentrations are at around 100 and under the lower boundary 202. The measured concentrations are outside of the boundary.

FIG. 4B illustrates a reactive diagram 300 of electrical signals using double reactive regions including the recess. The first reactive region and the second reactive region are separated by the recess such that the reactive agent is prevented from reflux back to the first reactive region. The electrical signal in the first reactive region is non-interfered by the reactive agent. The reactive agent is fully blended and reacted with the sample 5 in the second reactive region. The second reactive region can measure an accurate reactive signal. The recess can separate the first reactive region and the second reactive region such that a precision of a measurement is increased.

In FIG. 4B, most of the measured concentrations are within the boundary. For example, in FIG. 4B, for the actual concentration of around 150, the upper boundary 201 is at around 180 and the lower boundary 202 is at around 120. For the actual concentration of around 170, the measured concentrations are in a range from around 170 to around 140. The measured concentrations are within the boundary.

In some embodiments, a method for manufacturing a sensor strip 100, such as the biochemical sensor strip, includes some operations. The operations include providing the substrate 1. The recess 7 is formed in the substrate 1 such that the substrate 1 includes the first surface S25 and the second surface S27 separated by the recess 7. In some embodiments, the recess 7 is formed including the hydrophobic surface in the recess 7. The first electrode set 11 is disposed at the first surface S25. The second electrode set 12 is disposed at the second surface S27.

The insulation layer 2 is formed on the substrate 1. The insulation layer 2 includes the opening as the reactive zone 20 to expose the recess 7, the first surface 25, or the second surface 27.

The insulation layer 2 is formed on the substrate 1 such that the hydrophilic surface is over at least one of the first surface S25 or the second surface S27 by a predetermined height, such as the height H20.

The covering layer 3 is formed including the hydrophilic surface over the substrate 1. The covering layer 3 is formed on top of the insulation layer 2.

The present disclosure relates to the sensor strip 100 having two independent reactive areas such as the first reactive region 25 and the second reactive region 27. When a major reactive area performs its electrochemical reaction, the other minor reactive area is capable of measuring a factor which allows correcting of the analyte concentration detected in the major reactive area so as to obtain a higher accuracy of analyte concentration in the electrode strips and sensor strips.

In accordance with an embodiment of the present disclosure, when the major reactive area is configured to measure blood sugar, the minor reactive area is configured to detect an interfering factor for correcting the readings of blood sugar. The interfering factor is selected, but not limited, from hematocrit, triglyceride, cholesterol, uric acid, maltose, galactose, ascorbic acid, acetaminophenol, L-3,4-dihydroxyphenylalanine and dopamine.

In accordance with another embodiment of the present disclosure, when the major reactive area is configured to measure cholesterol, the minor reactive area is configured to detect an interfering factor for correcting the readings of cholesterol. Such an interfering factor is selected, but not limited, from hematocrit, hemoglobin, ascorbic acid, and methyl-3,4-dihydroxyphenylalanine.

In accordance with another embodiment of the present disclosure, when the major reactive area is configured to measure uric acid, the minor reactive area is configured to detect an interfering factor for correcting the readings of uric acid. Such an interfering factor is selected, but not limited, from hematocrit, hemoglobin, bilirubin and methyl-3, 4-dihydroxyphenylalanine.

In accordance with another embodiment of the present disclosure, when the major reactive area is configured to measure hemoglobin, the minor reactive area is configured to detect an interfering factor for correcting the readings of hemoglobin. Such an interfering factor is selected, but not limited, from hematocrit.

In accordance with another embodiment of the present disclosure, when the major reactive area is configured to measure lactic acid, the minor reactive area is configured to detect an interfering factor for correcting the readings of lactic acid. Such an interfering factor is selected, but not limited, from hematocrit, ascorbic acid, acetaminophenol and dopamine.

Moreover, the present disclosure further provides a measurement system with hematocrit correction. The measurement system includes the sensor strip 100, and a sensor. In some embodiments, the first electrode set 11 is configured to measure an analyte concentration (such as the analyte concentration in the above-identified major reactive area). The second electrode 12 set is configured to measure hematocrit or interfering factors in the above-mentioned minor reactive area. Moreover, the sensor is configured to electrically connect with the sensor strip. The sensor includes a power source, a detector and a microprocessor. The power source is configured to simultaneously provide a direct current (DC) signal and either an alternating current (AC) signal or an AC with DC offset signal. The DC signal is transmitted to either the first electrode set or the first electrode layer. Either the AC signal or the AC with DC offset signal is transmitted to the second electrode set 12. The detector is configured to detect a first reactive value in response to the analyte concentration and a second reactive value in response to the hematocrit concentration. The microprocessor is configured to calculate a hematocrit-corrected analyte concentration in response to the first reactive value and the second reactive value.

In the present disclosure, the sensor strip can avoid cross-contamination of sample liquids in two separated reactive regions so as to be suitable for domestic usage and quick diagnosis. Although the present disclosure is disclosed in the above-identified embodiments, which do not limit the present disclosure, persons having ordinary skill in the art, without departing from the spirit and scope of the present disclosure, may modify or amend accordingly. Therefore, the protection scope of the present disclosure is based on the appended claims.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, and composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A sensor strip, comprising:
a substrate comprising a first surface, a second surface, a recess between the first surface and the second surface, and a third surface in the recess;
a first electrode set disposed on top of the first surface;
a second electrode set disposed on top of the second surface; and
a covering layer comprising a covering surface facing the substrate;
wherein the third surface is hydrophobic and the covering surface is hydrophilic.

2. The sensor strip of claim 1, further comprising an insulation layer disposed between the covering layer and the substrate, the insulation layer comprising an opening, an aperture, a lateral side and a backside, and the opening being between the lateral sides and between the aperture and the backside.

3. The sensor strip of claim 2, wherein the substrate comprises a recess length between the first surface and the second surface, the lateral side comprises a side length, and a ratio between the side length and the recess length is from around 10 to around 5.

4. The sensor strip of claim 2, wherein the substrate comprises a recess length from the first surface to the second surface, and the recess length is variable across the recess.

5. The sensor strip of claim 2, wherein the substrate comprises a first edge between the first surface and the third surface, and the first edge comprises a protruding portion protruding toward the aperture or the backside.

6. The sensor strip of claim 2, wherein the substrate comprises a first edge between the first surface and the third surface, and the first edge comprises a portion extending beyond at least one of the lateral sides such that the insulation layer is partially over the recess.

7. The sensor strip of claim 1, wherein the substrate comprises a region having a region volume above the first surface and under the covering surface, the region volume is between the first surface and the second surface, the recess has a recess volume surrounded by the third surface and below the first surface, and a ratio between the region volume and the recess volume being from around 1 to around 3.

8. The sensor strip of claim 1, wherein at least one of the first surface and the second surface is hydrophilic.

\* \* \* \* \*